United States Patent [19]

Ide et al.

[11] Patent Number: 6,019,909
[45] Date of Patent: Feb. 1, 2000

[54] FLUORINATED HYDROCARBON COMPOUND AND PROCESS FOR ITS PREPARATION, AND REFRIGERATOR OIL AND MAGNETIC RECORDING MEDIUM LUBRICANT

[75] Inventors: Satoshi Ide; Katsuki Fujiwara; Masayuki Yamana; Yoshitaka Honda; Ikuo Yamamoto; Fumihiko Yamaguchi; Eiji Seki; Tatsuya Otsuka, all of Settsu; Satoshi Ishida, Sakai, all of Japan

[73] Assignee: Daikin Industries, Ltd., Osaka, Japan

[21] Appl. No.: 08/492,041

[22] PCT Filed: Jan. 21, 1991

[86] PCT No.: PCT/JP94/00084

§ 371 Date: Jul. 21, 1995

§ 102(e) Date: Jul. 21, 1995

[87] PCT Pub. No.: WO94/17023

PCT Pub. Date: Aug. 4, 1994

[30] Foreign Application Priority Data

Jan. 22, 1993 [JP] Japan ................................. 5-009035

[51] Int. Cl.[7] .......................... C10M 105/54; C07C 43/12
[52] U.S. Cl. ............................ 252/70; 568/683; 568/673; 568/671; 568/615; 208/18
[58] Field of Search ..................... 568/615, 671, 568/673, 674, 676, 677, 683; 208/18; 252/70, 71

[56] References Cited

U.S. PATENT DOCUMENTS

| | | | |
|---|---|---|---|
| 2,409,274 | 10/1946 | Hanford | 260/614 |
| 2,973,389 | 2/1961 | Weissermel et al. | 260/615 |
| 3,278,615 | 10/1966 | Larsen | 260/652.5 |
| 3,897,502 | 7/1975 | Russell et al. | 260/614 F |
| 3,976,788 | 8/1976 | Regan | 424/342 |
| 4,357,282 | 11/1982 | Anderson et al. | 260/544 F |

FOREIGN PATENT DOCUMENTS

| | | |
|---|---|---|
| 0 293 864 A2 | 12/1988 | European Pat. Off. . |
| 0293864 | 12/1988 | European Pat. Off. . |
| 0538719 | 2/1994 | European Pat. Off. . |
| 90/07562 | 7/1990 | WIPO . |
| WO 90/07562 | 7/1990 | WIPO . |
| 92/08774 | 5/1992 | WIPO . |
| WO 92/08774 | 5/1992 | WIPO . |

OTHER PUBLICATIONS

Sievert et al. –"Synethsis of perfluornated . . . ", Journal of Fluorine Chem., (1991).

"Synthesis of Perfluorinated Ethers by an Improved Solution Phase Direct Fluorination Process", Sievert et al, *Journal of Fluorine Chemistry*, vol. 53, 1991, pp. 397–417.

CA abstract 96:210105. 1982. Corresponds to Koller et al., Anal. Chem. (1982), 54(3), pp. 529–533.

CA abstract 95:186793. 1981. Corresponds to Yanagida et al., Bull Chem. Soc. Jpn. (1981), 54(4), pp. 1151–1158.

CA abstract 104:90001. 1986. Corresponds to Ito et al., JP 60139751.

CA abstract 98:97840. 1983. Corresponds to Glugla, J. Electrochem. Soc. (1983), 130(1), pp. 113–114.

*Primary Examiner*—John Kight
*Assistant Examiner*—Charanjit S. Aulakh
*Attorney, Agent, or Firm*—Larson & Taylor

[57] ABSTRACT

A novel fluorinated hydrocarbon compound containing an oxygen or sulfur atom in its molecule, produced by the nucleophilic reaction of a fluorine compound with a hydrocarbon compound. This compound is useful as a lubricant for various applications and particularly excellent as an oil for refrigerators wherein hydrochlorofluorocarbon is used as the refrigerant and as a magnetic recording medium lubricant.

16 Claims, No Drawings

FLUORINATED HYDROCARBON COMPOUND AND PROCESS FOR ITS PREPARATION, AND REFRIGERATOR OIL AND MAGNETIC RECORDING MEDIUM LUBRICANT

This application is a 371 of PCT/JP94/00084 filed Jan. 21, 1994 now WO94/17023 published Aug. 4, 1994.

FIELD OF THE INVENTION

The present invention relates to a novel compound which is usable generally as a lubricant and a process for preparing the compound, and more particularly to a fluorinated hydrocarbon compound containing an oxygen or sulfur atom in its molecule and useful as a refrigerating machine oil or as a lubricant for magnetic recording media.

The invention also concerns with the use of said fluorinated hydrocarbon compound, and more particularly with a refrigerating machine oil and a lubricant for magnetic recording media.

The term "refrigerating machine" used herein includes heat pumps.

BACKGROUND ART

Refrigerating Machine Oil

Heretofore known as refrigerating machine oils are mineral oils such as paraffinic oils, naphthenic oils and the like and synthetic oils such as alkylbenzene oils, ester oils and the like. These oils are used chiefly for refrigerating machines which employ trichlorofluoromethane (R-11), dichlorodifluoromethane (R-12) or the like as a refrigerant. In recent years, however, it has been suggested that chlorine-containing fully halogenated hydrocarbons such as R-11 or R-12 released into the atmosphere would deplete the stratospheric ozone layer, thereby inflicting a serious adverse influence on the ecosystem including humans on earth. Consequently an international agreement calls for the restriction of consumption and production of specific flons such as R-11 and R-12.

It has been proposed to use $CH_2FCF_3$ (R-134a) or like hydrogen-containing fluorinated hydrocarbons as a refrigerant substituting for R-11 or R-12. The proposed hydrocarbons are unlikely to deplete the ozone layer but poorly compatible with conventional refrigerator oils. Because of this defect, when the hydrogen-containing fluorinated hydrocarbon is used as a refrigerant in a refrigerator together with a conventional refrigerator oil, the refrigerator is made inoperative in a short time due to the lowered durability of a compressor, and the refrigerator capacity and coefficient of performance are significantly decreased.

In view of said problem, fluorine-containing oils may be used as a refrigerator oil since the oils are considered highly compatible with hydrogen-containing fluorinated hydrocarbons. These compounds are commercially available under the trade names "Fomblin" (product of Montefluos Co., Ltd.), "Krytox" (product of E.I. du Pont de Nemours & Co., Inc.), "Demnam" (product of Daikin Industries Ltd.), etc. The compounds have repeating units of the following formulas as the main structure

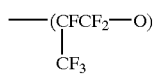

$$—(CFCF_2—O)_n—(CF_2—O)_m—$$
$$|$$
$$CF_3$$

wherein n and m are each an integer of 1 or more.

However, these known fluorine-containing oils are not necessarily fully compatible with refrigerants. This is presumably because these fluorine-containing oils contain little or no hydrogen in the structure. Further it is difficult to use these fluorine-containing oils for commercial purposes since the monomers corresponding to said repeating units in the structure are expensive.

When said hydrogen-containing fluorinated hydrocarbon is used as a refrigerant, fluorine- and hydrogen-containing oils are effectively used as a refrigerator oil in order to improve the compatibility between the refrigerant and refrigerator oil. Consequently the development of an expedient process for producing the fluorine- and hydrogen-containing oil is thought important to realize their use.

Fluorine- and hydrogen-containing oils are disclosed in Japanese Unexamined Patent Publications No. 205491/1991 and No. 7798/1991, etc. The disclosed oils, however, have drawbacks. For example, the oils contain, as the basic unit, a compound having a perfluoropolyether bond and the monomer used as the starting material is expensive. Moreover, because the fluorine-containing moiety of the monomer is basically COF-terminated, the reaction product of the monomer with a hydrocarbon compound is an ester and susceptible to hydrolysis. On the other hand, when a compound other than an ester is prepared, it is necessary to transform the end group —COF of the fluorine-containing compound to —$CH_2OH$, for example, by reduction reaction. Consequently, the reaction requires a multi-step procedure. Since the refrigerator oil thus prepared is expensive, it may be difficult to realize the commercial use of the refrigerator oil. The polyester-based compounds disclosed in Japanese Unexamined Patent Publications No. 128991/1991 and No. 179091/1991, etc. are reportedly highly compatible with R-134a, but are significantly hygroscopic and prone to hydrolysis or like decomposition because of the ester group present in the compound, posing a problem of durability.

Lubricant for Magnetic Recording Media

To improve the travelling stability and the durability of magnetic recording media, a method has been proposed which is to incorporate a lubricant into a magnetic layer or to coat a thin magnetic layer with a lubricant by coating methods such as dipping or spin coating. For example, the fluorine-containing polyether and the like described in Japanese Unexamined Patent Publication No. 113130/1986 are known as such lubricant.

In preparing a coating composition using said fluorine-containing polyether, the polyether is not fully dispersed in a common hydrocarbon-based organic solvent. Consequently the lubricant is readily removed from the coated magnetic layer by sliding contact of the recording media with the magnetic head, thereby making the magnetic recording media unsatisfactory in the abrasion resistance and durability.

Some fluorine-containing solvents are capable of fully dissolving fluorine-containing polyethers. Yet common solvents such as trichlorotrifluoroethane can no longer be used because of the recent problem of ozone layer depletion. Other fluorine-containing solvents (such as $C_6F_{14}$) considered free of ozone layer depletion problem are expensive although able to dissolve conventional fluorine-containing polyethers. Further these solvents reportedly contribute to global warming and thus their use requires great care.

OBJECTS OF THE INVENTION

It is an object of the present invention to provide a novel compound which is advantageous in the high compatibility with hydrogen-containing halogenated hydrocarbons and in the good stability, the compound being useful as an oil in a refrigerating machine using a hydrogen-containing halogenated hydrocarbon as a refrigerant, and a process for preparing the compound.

It is another object of the invention to provide a novel compound which is soluble in common organic solvents and which is useful as a lubricant for magnetic recording media, and a process for preparing the compound.

It is a further object of the invention to provide a refrigerating machine oil and a lubricant for magnetic recording media for which said novel compound is used.

DISCLOSURE OF THE INVENTION

The novel compounds of the present invention are the fluorinated hydrocarbon compounds represented by the formulas (I) to (V) (the symbols which represent the substituents and values in the formulas are described later in each paragraph).

Formula (I)

$$\begin{array}{c}R^1\\ \diagdown\\ R^3\end{array}C=C\begin{array}{c}R^2\\ \diagup\\ XR^4\end{array}$$

Formula (II)
$(R^5O)_a R^6$

Formula (III)
$(R^{10}OCH_2)_n R^{12}(CH_2OR^{11})_m$

Formula (IV)

$$R^{16}O(C_mH_{2m-1}O)_n(C_mH_{2m-1}O)_n-R^{19}$$
$$\phantom{R^{16}O(}|\phantom{C_mH_{2m-1}O)_n(}|$$
$$\phantom{R^{16}O(}OR^{17}\phantom{H_{2m-1}O)_n(}OR^{18}$$

Formula (V)

$$R^{16}O(CH_2CHCH_2O)_n-$$
$$\phantom{R^{16}O(C}|$$
$$\phantom{R^{16}O(}OR^{17}$$
$$\phantom{R^{16}O(CH_2CHCH_2O)}-(CH_2CHCH_2O)_n-R^{19}$$
$$\phantom{R^{16}O(CH_2CHCH_2O)}\phantom{-(CH_2CHC}|$$
$$\phantom{R^{16}O(CH_2CHCH_2O)}\phantom{-(CH_2CH}OR^{18}$$

The compounds of the present invention will be described below, respectively on their structures and processes for preparing them.

Present Compound of the Formula (I)

$R^1$, $R^2$, and $R^3$ in the formula (I) are each a fluorine atom, a partly or fully fluorinated, straight- or branched-chain alkyl or alkenyl group having 1 to 30 carbon atoms, preferably 1 to 10 carbon atoms, more preferably 1 to 5 carbon atoms (which may be partly halogenated with a halogen other than a fluorine).

The term "partly or fully fluorinated" used herein refers to substituents with a structure wherein the hydrogen atoms of the alkyl or alkenyl group are partly or all substituted by a fluorine atom or atoms. The term "which may be partly halogenated with a halogen other than a fluorine" is used to include substituents with a structure wherein the remaining hydrogen atom or atoms of the partly fluorinated alkyl or alkenyl group are partly or all halogenated with a halogen atom or atoms other than a fluorine atom.

Examples of substituents represented by $R^1$, $R^2$ and $R^3$ are straight- or branched-chain fluoroalkyl groups having a saturated structure, straight- or branched-chain fluoroalkenyl groups having an unsaturated structure, etc.

Among the compounds of the formula (I) (which may be hereinafter referred to as "compound (I)"), the compounds containing, as the substituents of $R^1$, $R^2$ and $R^3$, a fluoroalkyl or fluoroalkenyl group having a fluorine/carbon atomic ratio of at least 0.6, preferably at least 1, more preferably at least 1.5 are suitable for use as a refrigerating machine oil and as a lubricant for magnetic recording media.

Specific examples of substituents represented by $R^1$, $R^2$ and $R^3$ are given below. These substituents are preferred in that starting materials are easily available in commercial manufacture. However, the invention is not limited to them.

F—
$CF_3(CF_2)_n$— (n=integer of 0–2)
$(CF_3)_2CF(CF_2)_m$— (m=integer of 0–2)

$R^4$ in the formula (I) is a straight- or branched-chain alkyl or alkenyl group having 1 to 30 carbon atoms, preferably 5 to 25 carbon atoms, more preferably 10 to 20 carbon atoms (which may be partly halogenated with a halogen) or a polyether group having 2 to 500 carbon atoms, preferably 10 to 300 carbon atoms, more preferably 20 to 200 carbon atoms (which may be partly halogenated).

The term "which may be partly halogenated" is used herein to include substituents with a structure wherein the hydrogen atoms of the alkyl, alkenyl or polyether group are partly substituted by halogen atoms. The substituents represented by $R^4$ include those with a structure wherein the hydrogen atoms of the alkyl, alkenyl or polyether group are partly substituted by a substituent(s) other than a halogen atom. Examples of other substituents than halogen atoms are hydroxyl, thiol, alkoxy, nitrile, nitro, ether, thioether, ester, carbonyl, sulfonyl, sulfinyl, carboxyl, carboxylate, amino, thiocarbamate, amide, imide, phosphine, phosphorous ester, etc.

A polyalkylene glycol having the end of its molecule modified with an alkoxy group can be used as the starting material (precursor) useful for forming the polyether group (polyalkylene glycol group) as the substituent of $R^4$. Suitable polyalkylene glycols for use as the starting material are those having a kinematic viscosity at 40° C. of 1 to 500 cst, preferably 3 to 350 cst, more preferably 5 to 200 cst.

Specific examples of substituents represented by $R^4$ are given below. These groups are preferred in that starting materials are easily available in commercial manufacture. However, the present invention is not limited to them.

$C_nH_{2n+1}$— (n=integer of 10–30)
$C_mH_{2m-1}$— (m=integer of 10–30)
$C_hH_{2h-3}$— (h=integer of 10–30)
$CH_3(OCH_2CH_2)_l$— (l=integer of 1–100)

$$CH_3(OCH_2CH)_k-$$
$$\phantom{CH_3(OCH_2C}|$$
$$\phantom{CH_3(OCH_2}CH_3$$

(k=integer of 1–100)

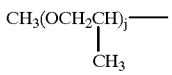

(j=integer of 1–100)

X in the formula (I) is an oxygen atom or a sulfur atom.

Process for Preparing the Compound (I)

The compound (I) of the present invention can be prepared by various processes, typically by the reaction represented by the following reaction formula.

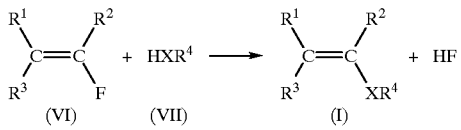

wherein $R^1$, $R^2$, $R^3$, $R^4$ and X have the same meaning as in the formula (I) and are as defined above for the formula (I).

The starting compound (VI) can be selected according to a combination of substituents represented by $R^1$, $R^2$ and $R^3$ in the contemplated compound (I). Specific examples are shown below. These examples are easily available and thus preferred and do not limit the invention.

$CF_3CF=CF_2$ (hexafluoropropene)

$(CF_3)_2CFCF=CFCF_3$ (hexafluoropropene diner, D-1)

$(CF_3)_2C=CFCF_2CF_3$ (hexafluoropropene diner, D-2)

$(CF_3)_2CFCF=C(CF_3)CF_2CF_2CF_3$ (hexafluoropropene trimer, T-1)

$((CF_3)_2CF)_2C=CFCF_3$ (hexafluoropropene trimer, T-1)

The starting compound (VII) can be selected according to a combination of substituents represented by $R^4$ and X in the contemplated compound (I). Specific examples are given below. These examples are easily available and thus preferred. The invention, however, is not limited to the examples.

Straight- or branched-chain higher alcohols $n-C_{10-20}H_{21-41}OH$ $i-C_{10-20}H_{21-41}OH$ etc.

(These examples include pure products of specific one species and mixtures of compounds which differ from each other in the number of carbon atoms.)

Straight- or branched-chain higher alkenyl alcohols $n-C_{10-20}H_{19-39}OH$ $i-C_{10-20}H_{19-39}OH$ $n-C_{10-20}H_{17-37}OH$ $i-C_{10-20}H_{17-37}OH$ etc.

(These examples include pure products of specific one species and mixtures of compounds which differ from each other in the number of carbon atoms.)

Coconut alkyl alcohols

Straight- or branched-chain higher thiols $n-C_{10-20}H_{21-41}SH$ $i-C_{10-20}H_{21-41}SH$ etc.

(These examples include pure products of specific one species and mixtures of compounds which differ from each other in the number of carbon atoms.)

(Terminus-modified) polyethylene glycol (Terminus-modified) polypropylene glycol (Terminus-modified) polybutylene glycol The reaction can be performed in the presence or the absence of a solvent. The amount of the solvent used is 0.1 to 100 times, preferably 0.5 to 10 times, more preferably 1 to 5 times, the total amount by volume of the starting compound (VI) and the starting compound (VII). Examples of usable solvents are aprotic polar solvents such as methyl ethyl ketone, acetone, DMF, DMSO, NMP, sulfolane, diglyme, triglyme, ether, THF, chloroform, dichloromethane, etc.

In the reaction, a basic catalyst can be used as a catalyst or as a scavenger for removing HF produced as a by-product. The basic catalyst is used in an amount of 0.001 to 10 equivalents, preferably 0.01 to 5 equivalents, more preferably 0.1 to 2 equivalents, based on any one of the starting compounds (VI) and (VII). Examples of the basic catalyst are inorganic bases such as KOH, NaOH, $K_2CO_3$, $Na_2CO_3$, etc. and organic bases such as triethylamine, tributylamine, etc.

The reaction temperature is −10 to 200° C., preferably 0 to 150° C., more preferably 0 to 100° C. The reaction pressure is 0 to 50 kg/cm²G, preferably 0 to 20 kg/cm²G, more preferably 0 to 10 kg/cm²G. The reaction time is 30 minutes to 100 hours, preferably 2 to 50 hours.

The ratio of the starting compound (VI) and the starting compound (VII) to be used in the reaction, namely a (VI)/(VII) equivalent ratio, is 0.01–20, preferably 0.5–10, more preferably 0.5–3.

In the reaction, the starting compounds can be simultaneously charged or can be supplied by adding dropwise one of the starting compounds to the other or by blowing one to the other.

There is no specific limitation on the method of treatment to be carried out after the reaction, i.e. the method for the recovery of the compound (I) from the reaction mixture. The compound can be purified by conventional methods. Stated more specifically, the reaction mixture is quenched in a large quantity of water and extracted with a water-immiscible solvent (such as CFC 113 (hereinafter S-3), dichloromethane, chloroform, etc.). The extract is washed with an acid, an alkali, a saturated aqueous solution of sodium chloride or the like, and dried over anhydrous sodium sulfate or anhydrous magnesium sulfate. After filtration, the solvent is distilled off from the filtrate at reduced pressure, whereby the compound (I) can be recovered. When required, the obtained product can be purified by vacuum distillation, column chromatography or the like.

Present Compound of the Formula (II)

The symbol d in the formula (II) is 1 or 2.

$R^5$ in the formula (II) is a partly or fully fluorinated, straight- or branched-chain alkyl, alkenyl or alkoxyalkyl group having 1 to 50 carbon atoms, preferably 1 to 35 carbon atoms, more preferably 2 to 26 carbon atoms (which may be partly halogenated with a halogen other than a fluorine and may have 1 to 3 OH groups in the structure) or a partly or fully fluorinated fluoropolyether group having 2 to 700 carbon atoms, preferably 3 to 800 carbon atoms, more preferably 5 to 150 carbon atoms (which may be partly halogenated with a halogen other than a fluorine, may have 1 to 3 unsaturated bonds in the structure and may include an ether bond or bonds in the side chain).

The term "partly or fully fluorinated" used herein refers to (i) substituents with a structure wherein the hydrogen atoms of the alkyl, alkenyl or alkoxyalkyl group are partly or all substituted by a fluorine atom or atoms, or (ii) a fluoropolyether group containing at least one fluorine atom in the molecule. The term "which may be partly halogenated with a halogen other than a fluorine" used herein refers to (i) substituents with a structure wherein the remaining hydrogen atoms of the partly fluorinated alkyl, alkenyl or alkoxyalkyl group are partly or all substituted by a halogen atom or atoms other than a fluorine atom, or (ii) a fluoropolyether group containing at least one halogen atom other than a fluorine atom in the molecule, and the term "which may have 1 to 3 OH groups in the structure" used herein refers to a structure wherein 1 to 3 hydrogen atoms are substituted by OH groups. The term "which may have 1 to 3 unsaturated bonds in the structure" is used herein to include an unsaturated fluoropolyether group having 1 to 3 carbon-carbon double bonds and triple bonds in total per substituent in the structure as well as a saturated fluoropolyether group (not having a carbon-carbon double bond or triple bond). The term "which may have an ether bond or bonds in the side chain" is used herein to include a fluoropolyether group having an ether bond or bonds in the side chain as well as one having an ether bond or bonds in the main chain.

Examples of substituents represented by $R^5$ are straight- or branched-chain fluoroalkyl groups or hydroxyfluoroalkyl groups having a saturated structure, straight- or branched-chain fluoroalkenyl groups or hydroxyfluoroalkenyl groups having an unsaturated structure, etc.

Among the compounds of the formula (II), the compounds containing, as the substituent of $R^5$, a fluoroalkyl, fluoroalkenyl, fluoroalkoxyalkyl or fluoropolyether group having a fluorine/carbon atomic ratio of at least 0.6, preferably at least 1, more preferably at least 1.5 are suitable for use as a refrigerating machine oil and as a lubricant for magnetic recording media.

Specific examples of substituents represented by $R^5$ are shown below. These substituents are preferred in that starting materials are readily available in commercial manufacture. However, the present invention is not limited to them.

$(CF_3)_2CF(CF_2CF_2)_nCH_2CH_2OCH_2CH(OH)CH_2—$ (n=integer of 0–10)

$CF_3CF_2(CF_2CF_2)_mCH_2CH_2OCH_2CH(OH)CH_2—$ (m=; integer of 0–10)

$H(CF_2CF_2)_lCH_2CH_2CH(OH)CH_2—$ (l=integer of 0–10)

$(CF_3)_2CF(CF_2CF_2)_kCH_2CH(OH)CH_2—$ (k=integer of 0–10)

$CF_3CF_2(CF_2CF_2)_jCH_2CH(OH)CH_2—$ (j=integer of 0–10)

$(CF_3)_2CF(CF_2CF_2)_aCH_2CH_2—$ (a=integer of 0–10)

$CF_3CF_2(CF_2CF_2)_bCH_2CH_2—$ (b=integer of 0–10)

$H(CF_2CF_2)_cCH_2—$ (c=integer of 0–10)

$HCF_2CF_2—$ $HCClFCF_2—$ $HCF_2CClF—$ $CF_3CFHCF_2—$ $CF_3CF=CF—$ $CF_2=CFCF_2—$ $CH_3CF_2—$ $(CF_3)_2CHCF_2—$ $HOC(CF_3)_2—$ $Cl(CF_2CClF)_iCFHCClF—$ (i=integer of 1–20)

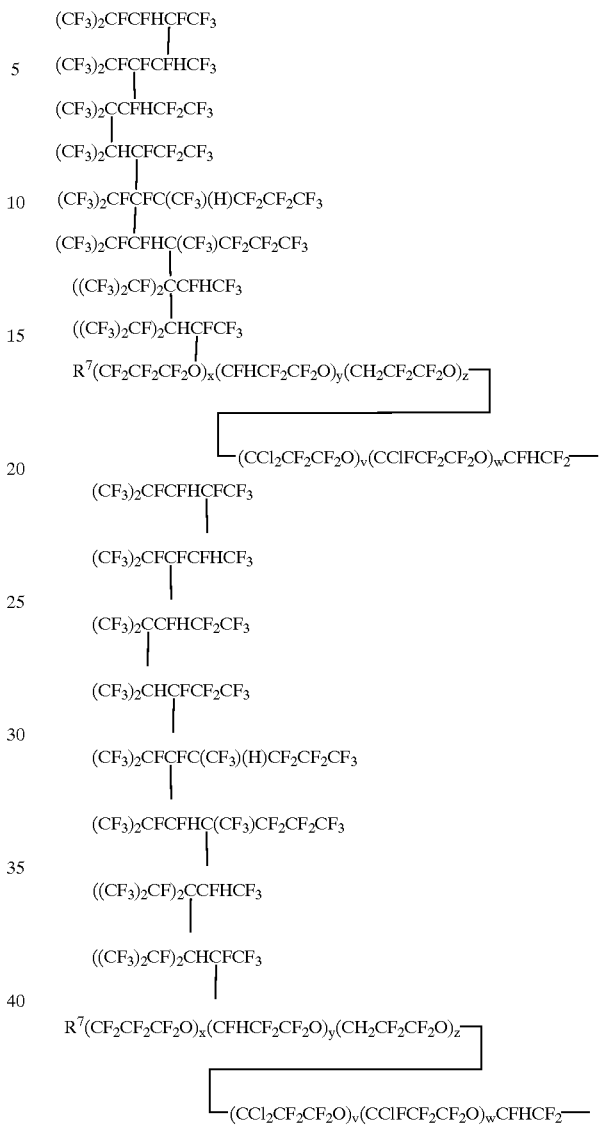

wherein x, y, z, v and w are each an integer of 0 to 100, provided that they can not be zero at the same time, and $R^7$ is a halogen atom or an alkoxy group having 1 to 3 carbon atoms (which may be partly or fully fluorinated), or $R^8(CF(CF_3)CF_2O)_p(CF_2CF_2O)_q(CF_2O)_rCFHCF_2—$ wherein p, q and r are each an integer of 0 to 100, provided that they can not be zero at the same time, and $R^8$ is a halogen atom or an alkoxy group having 1 to 3 carbon atoms (which may be partly or fully fluorinated).

The fluoropolyether group represented by $R^5$ can be formed using a fluoropolyether as the starting material (precursor) having, in the main chain structure, the corresponding perfluoropolyether, not fully fluorinated fluoropolyether, halogenated fluoropolyether partly substituted by other halogen atom or the like. Specific examples of fluoropolyethers usable as the starting material (manufacturers and trade names) are shown below. These examples are desirable to use because they are commercial products and easily available. Yet the invention is not limited to them.

"Demnam" (product of Daikin Industries Ltd.)
"Krytox" (product of E.I. du Pont de Nemours & Co., Inc.)
"Fomblin Y" (product of Montefluos Co., Ltd.)
"Fomblin Z" (product of Montefluos Co., Ltd.)
"Fomblin K" (product of Montefluos Co., Ltd.)
"Barierta" (product of NOK)

Preferred fluoropolyethers useful as the starting material are those having a fluorine/carbon atomic ratio of at least 0.6, preferably at least 1, more preferably at least 1.5.

When d in the formula (II) is 1, $R^6$ represents a monofunctional group, specifically a straight- or branched-chain alkyl group or alkenyl group having 1 to 30 carbon atoms, preferably 1 to 10 carbon atoms, more preferably 1 to 5 carbon atoms which may be partly halogenated or a polyether group having 2 to 500 carbon atoms, preferably 10 to 300 carbon atoms, more preferably 20 to 200 carbon atoms which may be partly halogenated.

The substituents represented by $R^6$ include those with a structure wherein the group is substituted by a substituent other than a halogen atom. Examples of substituents other than a halogen atom are hydroxyl, thiol, alkoxy, nitrile, nitro-ether, thioether, ester, carbonyl, sulfonyl, sulfinyl, carboxyl, carboxylate, amino, thiocarbamate, amide, imide, phosphine, phosphorous ester, etc.

When d in the formula (II) is 1, a polyalkylene glycol with the end of its molecule modified with an alkoxy group can be used as the starting material (precursor) useful for forming the polyether group (polyalkyleneglycol group) as the substituent of $R^6$. Suitable polyalkylene glycols for use as the starting material are those having a kinematic viscosity at 40° C. of 1 to 500 cst, preferably 3 to 350 cst, more preferably 5 to 200 cst.

Specific examples of monofunctional groups represented by $R^5$ are given below. These groups are preferred in that starting materials are easily available in commercial manufacture. However, the present invention is not limited to them.

$C_nH_{2n+1}$— (n=integer of 10–30)
$C_mH_{2m-1}$— (m=integer of 10–30)
$C_hH_{2h-3}$— (h=integer of 10–30)
$ClC_lH_{2l}$— (l=integer of 1–10)
$Cl(CH_2)_7CH=CH(CH_2)_8$—
$CH_3(OCH_2CH_2)_k$— (k=integer of 1–100)

$$CH_3(OCH_2CH)_j-\!\!\!\!\!-\!\!\!\!\!-\\ \phantom{CH_3(OCH_2CH)}|\\ \phantom{CH_3(OCH_2C}CH_3$$

(j=integer of 1–100)

$$CH_3(OCH_2CH)_i-\!\!\!\!\!-\!\!\!\!\!-\\ \phantom{CH_3(OCH_2CH)}|\\ \phantom{CH_3(OCH_2}CH_2CH_3$$

(i=integer of 1–100)

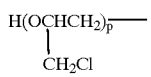

(p=integer of 1–100)

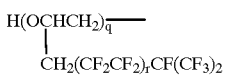

(q=integer of 1–100 and r=integer of 0–10)

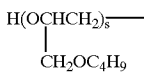

(s=integer of 1–100)

When d in the formula (II) is 2, $R^6$ represents a bifunctional group, specifically a straight- or branched-chain bifunctional alkyl group or bifunctional alkenyl group having 1 to 10 carbon atoms, or a bifunctional polyether group having 2 to 500 carbon atoms, preferably 10 to 300 carbon atoms, more preferably 20 to 200 carbon atoms. The substituents represented by $R^6$ include bifunctional groups with a structure wherein the hydrogen atoms are partly substituted by a halogen atom or atoms, and bifunctional groups with a structure wherein the hydrogen atoms are partly substituted by other substituents than a halogen atom. Examples of substituents other than halogen atoms are hydroxyl, thiol, alkoxy, nitrile, nitro, ether, thioether, ester, carbonyl, sulfonyl, sulfinyl, carboxyl, carboxylate, amino, thiocarbamate, amide, imide, phosphine, phosphorous ester, etc.

When d in the formula (II) is 2, a polyalkylene glycol having the end of its molecule modified with an alkoxy group can be used as the starting material (precursor) useful for forming the bifunctional polyether group (bifunctional polyalkylene glycol group) as the substituent of $R^6$. Suitable polyalkylene glycols for use as the starting material are those having a kinematic viscosity at 40° C. of 1 to 500 cst, preferably 3 to 350 cst, more preferably 5 to 200 cst.

Specific examples of bifunctional groups represented by $R^6$ are given below. These groups are preferred in that starting materials are easily available in commercial manufacture. However, the present invention is not limited to them.

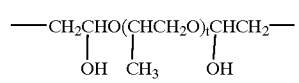

Process for Preparing the Compound (II)

The compound (II) can be prepared by various processes.

For example, when $R^5$ in the formula (II) is any of the substituents given below:

$HCF_2CF_2$—, $HCClFCF_2$—, $HCF_2CClF$—,
$CF_3CFHCF_2$—, $CF_3CF=CF$—,
$CF_2=CFCF_2$—, $CH_3CF_2$—, $(CF_3)_2CHCF_2$—, $HOC(CF_3)_2$—,

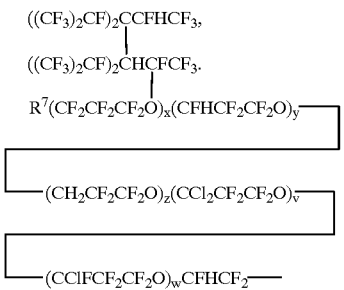

$Cl(CF_2CClF)_iCFHCClF$— (i=integer of 1–20).

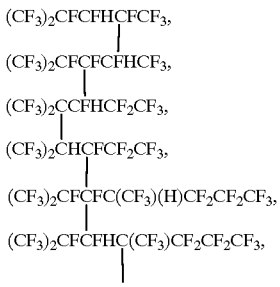

wherein x, y, z, v and w are each an integer of 0 to 100, provided that they can not be zero at the same time, $R^7$ is a halogen atom or an alkoxy group having 1 to 3 carbon atoms (which may be partly or fully fluorinated), or

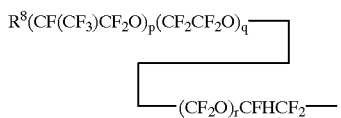

wherein p, q and r are each an integer of 0 to 100, provided that they can not be zero at the same time, $R^8$ is a halogen atom or an alkoxy group having 1 to 3 carbon atoms (which may be partly or fully fluorinated), and d in the formula (II) is 1 and $R^5$ is any of the following substituents:

$C_nH_{2n+1}$— (n=10–30),
$C_mH_{2m-1}$— (m=10–30),
$C_hH_{2h-3}$— (h=10–30),
$ClC_lH_{2l}$— (l=integer of 1–10)
$Cl(CH_2)_7CH=CH(CH_2)_8$—,
$CH_3(OCH_2CH_2)_k$— (k=integer of 1–100),

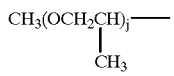

(j=integer of 1–100),

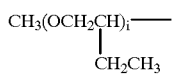

(i=integer of 1–100),

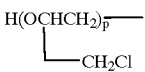

(p=integer of 1–100),

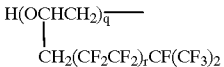

(q=integer of 1–100), or

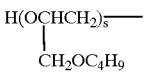

wherein s is an integer of 1 to 100, and r is an integer of 0 to 10, or d in the formula (II) is 2 and $R^6$ represents a substituent
—$(C_hH_{2h})$—(h=integer of 1–10)
the corresponding compound (II) can be prepared typically by the reaction of reaction formula (B) or reaction formula (C) given below:
Reaction Formula (B) (d=1 and $R^6$=monofunctional group)

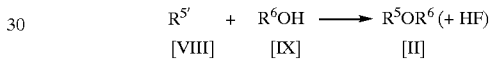

Reaction Formula (c) (d=2 and $R^6$=bifunctional group)

The starting compound (VIII) represented by $R^{5'}$ includes, for example, fluoroolefins and fluoroketones as exemplified below
$CF_2=CF_2$
$CClF=CF_2$
$CF_3CF=CF_2$
$CH_2=CF_2$
$(CF_3)_2C=CF_2$
$(CF_3)_2C=O$
$Cl(CF_2CClF)_iCF=CClF$ (i=integer of 1–20)
$(CF_3)_2CFCF=CFCF_3$
$(CF_3)_2C=CFCF_2CF_3$
$(CF_3)_2CFCF=C(CF_3)CF_2CF_3$
$((CF_3)_2CF)_2C=CFCF_3$
$(CF_3)_2C=C(CF_2CF_3)CF(CF_3)_2$

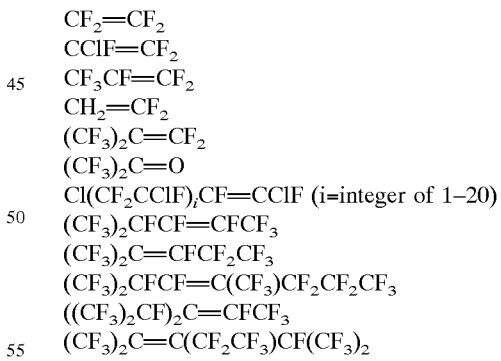

wherein x, y, z, v and w are each an integer of 0 to 100, provided that they can not be zero at the same time, and $R^7$ is a halogen atom or an alkoxy group having 1 to 3 carbon atoms (which may be partly or fully fluorinated), or $R^8(CF(CF_3)CF_2O)_p(CF_2CF_2O)_q(CF_2O)_rCF=CF_3$ wherein p, q and r are each an integer of 0 to 100, provided that they can not be zero at the same time, $R^8$ is a halogen atom or an alkoxy group having 1 to 3 carbon atoms (which may be partly or fully fluorinated), and $R^5$ and $R^6$ are as defined above.

The starting compound (VIII) can be selected according to the substituents represented by $R^{5'}$ in the contemplated compound (II). Numerous compounds can be specifically exemplified and specific examples include fluoroolefins and fluoroketones shown below. These compounds are preferred because they are easily available. Yet the invention is not limited to them.

$CF_2=CF_2$ (tetrafluoroethyrene)

$CClF=CF_2$ (chlorotrifluoroethyrene)

$CF_3CF=CF_2$ (hexafluoropropene)

$CH_2=CF_2$ (vinylidene fluoride)

$(CF_3)_2C=CF_2$ (octafluoroisobutene)

$(CF_3)_2C=O$ (hexafluoroacetone)

$Cl(CF_2CClF)_{1-20}CF=CClF$ $(CF_3)_2CFCF=CFCF_3$ (hexafluoropropene dimer, D-1)

$(CF_3)_2C=CFCF_2CF_3$ (hexafluoropropene dimer, D-2)

$(CF_3)_2CFCF=C(CF_3)CF_2CF_2CF_3$ (hexafluoropropene trimer, T-1)

$((CF_3)_2CF)_2C=CFCF_3$ (hexafluoropropene trimer, T-2)

$C_3F_7OCF=CF_2$ $C_3F_7OCF(CF_3)CF_2OCF=CF_2$ $C_3F_7O(CF(CF_3)CF_2O)_2CF=CF_2$

The starting compound (IX) and the starting compound (IX') can be selected according to the substituent represented by $R^6$ in the contemplated compound (II). Typical examples are shown below:

Compound (IX)

Higher (branched-chain) alcohols n-$C_{10-20}H_{21-41}$OH i-$C_{10-20}H_{21-41}$OH etc.

(The examples include pure products of specific single species and mixtures of compounds which differ in the number of carbon atoms.)

Higher (branched-chain) alkenyl alcohols n-$C_{10-20}H_{19-39}$OH i-$C_{10-20}H_{19-39}$OH n-$C_{10-20}H_{17-37}$OH i-$C_{10-20}H_{17-37}$OH etc.

(The examples include pure products of specific single species and mixtures of compounds which differ in the number of carbon atoms.)

Coconut alkyl alcohols $ClC_2H_4OH$ $Cl(CH_2)_7CH=CH(CH_2)_8OH$ etc.

Compound (IX')

(Terminus-modified) polyethylene glycol (Terminus-modified) polypropylene glycol (Terminus-modified) polybutylene glycol

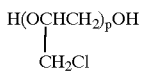

(p=integer of 1–100)

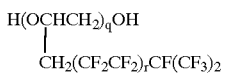

(q=integer of 1–100, r=integer of 1–10)

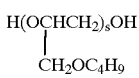

(s=integer of 1–100)

These reactions can be conducted in the presence or the absence of a solvent. The amount of the solvent used is 0.1 to 100 times, preferably 0.5 to 10 times, more preferably 1 to 5 times, the total amount by volume of the starting compound (VIII) and the starting compound (IX) or the starting compound (IX'). Examples of usable solvents are aprotic polar solvents such as methyl ethyl ketone, acetone, DMF, DMSO, NMP, sulfolane, diglyme, triglyme, ether, THF, chloroform, dichloromethane, etc.

In these reactions, a basic catalyst can be used as a catalyst or as a scavenger for removing HF produced as a by-product. The basic catalyst is used in an amount of 0.001 to 10 equivalents, preferably 0.01 to 5 equivalents, more preferably 0.1 to 2 equivalents, based on any one of the starting compounds (VIII), (IX) and (IX'). Examples of the basic catalyst are inorganic bases such as KOH, NaOH, $K_2CO_3$, $Na_2CO_3$, etc. and organic bases such as triethylamine, tributylamine, etc.

The reaction temperature for said reactions is −10 to 200° C., preferably 0 to 150° C., more preferably 10 to 100° C. The reaction pressure is 0 to 50 kg/cm²G, preferably 0 to 20 kg/cm²G, more preferably 0 to 10 kg/cm²G. The reaction time is 30 minutes to 100 hours, preferably 2 to 50 hours.

The ratio of the starting compound (VIII) and the starting compound (IX) or the starting compound (IX') to be used in the reactions, namely a (VIII)/(IX) equivalent ratio or (VIII)/(IX') equivalent ratio, is 0.01–20, preferably 0.5–10, more preferably 0.5–3.

In said reactions, the starting compounds can be simultaneously charged or can be supplied by adding dropwise one of the starting compounds to the other or by blowing one to the other. Yet the invention is not limited in this respect.

There is no specific limitation on the treatment method to be conducted after the reaction, namely the method for the recovery of the compound (II) from the reaction mixture. The compound can be purified by conventional methods. Stated more specifically, the reaction mixture is quenched in a large quantity of water and extracted with a water-immiscible solvent (such as S-3, dichloromethane, chloroform, etc.). The extract is washed with an acid, an alkali, a saturated aqueous solution of sodium chloride or the like, and dried over anhydrous sodium sulfate or anhydrous magnesium sulfate. After filtration, the solvent is distilled off at reduced pressure from the filtrate, whereby the compound (II) is recovered. When required, the obtained product can be purified by vacuum distillation, column chromatography or the like.

For example, when $R^5$ in the formula (II) is as defined above, d in the formula (II) is 1, and $R^6$ is any of the following substituents:

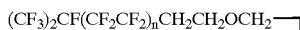
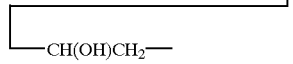

(n=integer of 0–10),

(m=integer of 0–10),
$H(CF_2CF_2)_lCH_2CH_2CH(OH)CH_2$— (l=integer of 0–10),

(k=integer of 0–10),
$CF_3CF_2(CF_2CF_2)_jCH_2CH(OH)CH_3$— (j=integer of 0–10),
$(CF_3)_2CF(CF_2CF_2)_aCH_2CH_2$— (a=integer of 0–10),
$CF_3CF_2(CF_2CF_2)_bCH_2CH_2$— (b=integer of 0–10) or
$H(CF_2CF_2)_cCH_2$— (c=integer of 0–10) or
or when d in the formula (II) is 2, and $R^{6'}$ represents the following substituent:

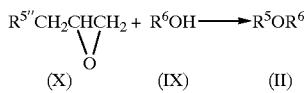

wherein t is an integer of 1 to 100, the corresponding compound (II) can be prepared typically by the reaction represented by the reaction formula (D) or (E) shown below.
Reaction Formula (D) (d=1 and $R^6$=monofunctional group)

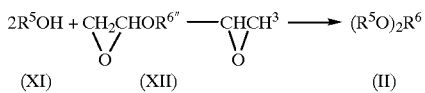

Reaction Formula (E) (d=2 and $R^6$=bifunctional group)

In the reaction formulas, $R^5$ represents the following substituents
$(CF_3)_2CF(CF_2CF_2)_aCH_2CH_2$— (a=integer of 0–10)
$CH_3CF_2(CF_2CF_2)_bCH_2CH_2$— (b=integer of 0–10)
$H(CF_2CF_2)_cCH_2$— (c=integer of 0–10)
$R^{5''}$ represents the following substituents
$(CF_3)_2CF(CF_2CF_2)_nCH_2CH_2O$— (n=integer of 0–10)

$CH_3CF_2(CF_2CF_2)_mCH_2CH_2O$— (m=integer of 0–10)
$H(CF_2CF_2)_lCH_2$— (l=integer of 0–10)
$(CF_3)_2CF(CF_2CF_2)_k$— (k=integer of 0–10)
$CF_3CF_2(CF_2CF_2)_j$— (j=integer of 0–10)
$R^6$ is as defined above, and $R^{6''}$ represents

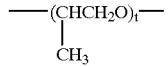

t=integer of 0–100)
The starting compound (IX) is defined as above.
Specific examples of the starting compound (X) are shown below. These compounds are preferred because of their ready availability and do not limit the invention.

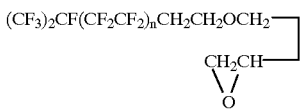

(n=integer of 0–10)

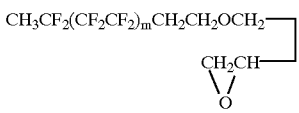

(m=integer of 0–10)

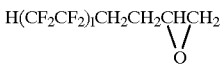

(l=integer of 0–10)

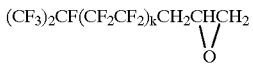

(k=integer of 0–10)

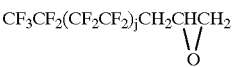

(j=integer of 0–10)
Specific examples of the starting compound (XI) are shown below. These compounds are preferred because of their ready availability but do not limit the invention.
$(CF_3)_2CF(CF_2CF_2)_aCH_2CH_2OH$ (a=integer of 0–10)
$CH_3CF_2(CF_2CF_2)_bCH_2CH_2OH$ (b=integer of 0–10)
$H(CF_2CF_2)_cCH_2OH$ (c=integer of 0–10)
Specific examples of the starting compound (XII) include

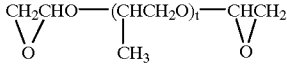

wherein t is an integer of 0 to 100. These compounds are preferred because of their ready availability but do not limit the invention.
These reactions can be conducted in the presence or the absence of a solvent. The amount of the solvent used is 0.1 to 100 times, preferably 0.5 to 10 times, more preferably 1 to 5 times, the total amount by volume of the starting compound (X) and the starting compound (IX) or the starting compound (XI) and the starting compound (XII). Examples of usable solvents are aprotic polar solvents such as methyl ethyl ketone, acetone, DMF, DMSO, NMP, sulfolane, diglyme, triglyme, ether, THF, chloroform, dichloromethane, etc.

In these reactions, a Lewis acid catalyst can be used as a catalyst. The Lewis acid catalyst is used in an amount of 0.001 to 10 equivalents, preferably 0.01 to 5 equivalents, more preferably 0.1 to 2 equivalents, based on the total amount of the starting compounds used. Specific examples of Lewis acid catalysts are boron trifluoride, adducts of boron trifluoride with ether, etc.

The reaction temperature for these reactions is −10 to 200° C., preferably 0 to 150° C., more preferably 10 to 100° C. The reaction pressure is 0 to 10 kg/cm$^2$G, preferably 0 to 5 kg/cm$^2$G, more preferably 0 to 2 kg/cm$^2$G. The reaction time is 30 minutes to 100 hours, preferably 2 to 50 hours.

The ratio of the starting compound (X) and the starting compound (IX) to be used or the ratio of the starting compound (XI) and the starting compound (XII) to be used, namely a (X)/(IX) equivalent ratio, or (XI)/(XII) equivalent ratio, is 0.01–20, preferably 0.5–10, more preferably 0.5–3.

In these reactions, the starting compounds can be simultaneously charged or can be supplied by adding dropwise one of the starting compounds to the other or by blowing one to the other. Yet the invention is not limited in this respect.

There is no specific limitation on the treatment method to be conducted after the reaction, namely the method for the recovery of the compound (II) from the reaction mixture. The compound can be purified by conventional methods. Stated more specifically, the reaction mixture is quenched in a large quantity of water and extracted with a water-immiscible solvent (such as S-3, dichloromethane, chloroform, etc.). The extract is washed with an acid, an alkali, a saturated aqueous solution of sodium chloride or the like, and dried over anhydrous sodium sulfate, or anhydrous magnesium sulfate. After filtration, the solvent is distilled off at reduced pressure from the filtrate, whereby the compound (II) is recovered. When required, the obtained product can be purified by vacuum distillation, column chromatography or the like.

Present Compound of the Formula (III)

The symbol n in the formula (III) is an integer of 0 to 2, m is an integer of 1 to 4, and $1 \leq n+m \leq 4$ $R^{10}$ in the formula (III) is a hydrogen atom, a partly or fully fluorinated, straight- or branched-chain alkyl, alkenyl or alkoxyalkyl group having 1 to 50 carbon atoms, preferably 1 to 35 carbon atoms, more preferably 2 to 26 carbon atoms (which may be partly halogenated with a halogen other than a fluorine and may have 1 to 3 OH groups in the structure) or a partly or fully fluorinated fluoropolyether group having 2 to 700 carbon atoms, preferably 3 to 300 carbon atoms, more preferably 5 to 150 carbon atoms (which may be partly halogenated with a halogen other than a fluorine, may have 1 to 3 unsaturated bonds in the structure and may have an ether bond or bonds in the side chain).

The term "partly or fully fluorinated" used herein refers to (i) substituents with a structure wherein the hydrogen atoms of the alkyl, alkenyl or alkoxyalkyl group are partly or all substituted by a fluorine atom or atoms or (ii) a fluoropolyether group containing at least one fluorine atom in the structure. The term "which may be partly halogenated with a halogen other than a fluorine" used herein refers to (i) substituents with a structure wherein the remaining hydrogen atoms of the partly fluorinated alkyl, alkenyl or alkoxyalkyl group are partly or all substituted by a halogen atom or atoms other than a fluorine atom, or (ii) a fluoropolyether group containing at least one halogen atom other than a fluorine atom in the structure, and the term "which may have 1 to 3 OH groups in the structure" used herein refers to a structure wherein 1 to 3 hydrogen atoms are substituted by OH groups. The term "which may have 1 to 3 unsaturated bonds in the structure" is used herein to include an unsaturated fluoropolyether group having 1 to 3 carbon—carbon double bonds and triple bonds in total per substituent in the structure as well as a saturated fluoropolyether group (not having a carbon-carbon double bond or triple bond). The term "which may have an ether bond or bonds in the side chain" is used herein to include a fluoropolyether group having an ether bond or bonds in the side chain as well as one having an ether bond or bonds in the main chain.

Examples of substituents represented by $R^{10}$ are straight- or branched-chain fluoroalkyl groups or hydroxyfluoroalkyl groups having a saturated structure, straight- or branched-chain fluoroalkenyl groups or hydroxyfluoroalkenyl groups having an unsaturated structure, etc.

Among the compounds of the formula (III), the compounds having as the substituent of $R^{10}$ a fluoroalkyl group, fluoroalkenyl group, fluoroalkoxyalkyl group or fluoropolyether group having a fluorine/carbon atomic ratio of at least 0.6, preferably at least 1, more preferably at least 1.5 are suitable for use as a refrigerating machine oil and as a lubricant for magnetic recording media.

Specific examples of substituents represented by $R^{10}$ are shown below. They are desirable because they are easily available in commercial manufacture, but do not limit the present invention.

H—

HCF$_2$CF$_2$—

HCClFCF$_2$—

HCF$_2$CClF—

CF$_3$CFHCF$_2$—

CF$_3$CF=CF—

CF$_2$=CFCF$_2$—

CH$_3$CF$_2$—

(CF$_3$)$_2$CHCF$_2$—

HOC(CF$_3$)$_2$—

Cl(CF$_2$CClF)$_i$CFHCClF— (i=integer of 1–20)

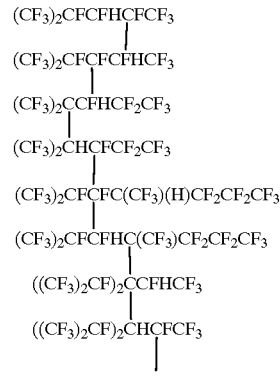

Process for Preparing the Compound (III)

The compound (III) can be prepared by various processes, typically by a 2-step reaction represented by the following reaction formula (F).

Reaction Formula (F)
First Reaction

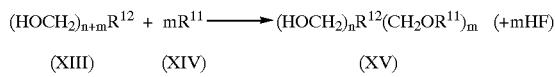

Second Reaction

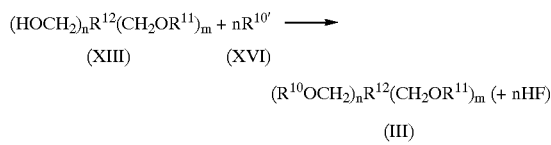

In the formula (F), n is an integer of 0 to 2, m is an integer of 1 to 4 and $1 \leq n+m \leq 4$.

$R^{10}$, $R^{11}$ and $R^{12}$ are as defined above.

The starting compound (XIV) represented by $R^{11'}$ can be selected according to the substituents represented by $R^{11}$ in the contemplated compound (III), and the starting compound (XVI) represented by $R^{10'}$ can be selected according to the substituents represented by $R^{10}$ in the contemplated compound (III). Specific examples include fluoroolefins and fluoroketones as exemplified below. They are preferred in view of their ready availability but do not limit the invention.

$CF_2=CF_2$
$CClF=CF_2$
$CF_3CF=CF_2$
$CH_2=CF_2$
$(CF_3)_2C=CF_2$
$(CF_3)_2C=O$
$Cl(CF_2CClF)_iCF=CClF$ (i=integer of 1–20)
$CF_3CF=CF_2$
$(CF_3)_2CFCF=CFCF_3$
$(CF_3)_2C=CFCF_2CF_3$
$(CF_3)_2CFCF=C(CF_3)CF_2CF_2CF_3$
$((CF_3)_2CF)_2C=CFCF_3(CF_3)_2C=C(CF_2CF_3)CF(CF_3)_2$

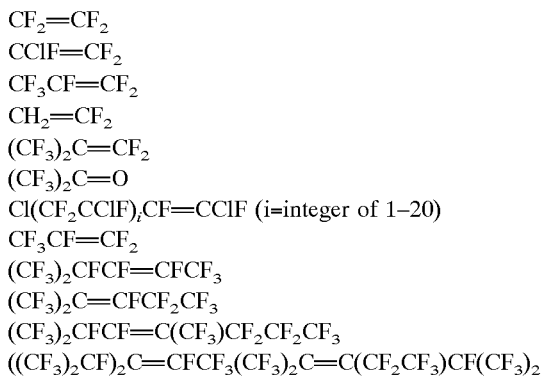

wherein x, y, z, v and w are each an integer of 0 to 100, provided that they can not be zero at the same time, $R^7$ is a halogen atom or an alkoxy group having 1 to 3 carbon atoms which may be partly or fully fluorinated, or $R^8(CF(CF_3)CF_2O)_p(CF_2CF_2O)_q(CH_2O)_rCF=CF_2$ wherein p, q and r are each an integer of 0 to 100, provided that they can not be zero at the same time, and $R^8$ is a halogen atom or an alkoxy group having 1 to 3 carbon atoms which may be partly or fully fluorinated.

The starting compound (XIII) includes various compounds differing from each other in the values of m and n, such as so-called hindered alcohols. They are preferred in view of their ready availability but do not limit the invention. Specific examples of the compound (XIII) are given below.

$(HOCH_2)_4C$
$(HOCH_2)_3CCH_3$
$(HOCH_2)_3CCH_2CH_3$
$(HOCH_2)_2C(CH_3)_2$
$HOCH_2C(CH_3)_3$ etc.

Numerous compounds are available as starting compounds (XIV) and (XVI) as set forth hereinbefore. Specific examples include fluoroolefins and fluoroketones given below. They are preferred in view of their ready availability but do not limit the invention.

$CF_2=CF_2$ (tetrafluoroethyrene)
$CClF=CF_2$ (chlorotrifluoroethyrene)
$CF_3CF=CF_2$ (hexafluoropropene)
$CH_2=CF_2$ (vinylidene fluoride)
$(CF_3)_2C=CF_2$ (octafluoroisobutene)
$(CF_3)_2C=O$ (hexafluoroacetone)
$Cl(CF_2CClF)_{1-20}CF=CClF$
$(CF_3)_2CFCF=CFCF_3$ (hexafluoropropene dimer, D-1)
$(CF_3)_2C=CFCF_2CF_3$ (hexafluoropropene dimer, D-2)
$(CF_3)_2CFCF=C(CF_3)CF_2CF_2CF_3$ (hexafluoropropene trimer, T-1)
$((CF_3)_2CF)_2C=CFCF_3$ (hexafluoropropene trimer, T-2)
$C_3F_7OCF=CF_2$
$C_3F_7OCF(CF_3)CF_2OCF=CF_2$
$C_3F_7O(CF(CF_3)CF_2O)_8CF=CF_2$ When the ratio of the starting compounds (XIV) and (XIII) to be used in the first reaction, namely a (XIV)/(XIII) equivalent ratio, is less than 1, or when the reaction time is shortened to terminate the reaction before its complete cease, there can be obtained a compound (XV) wherein $R^{10}$ in the formula (III) is a hydrogen atom.

The compound (III) wherein the substituent of $R^{10}$ structurally differs from the substituent of $R^{11}$ can be obtained using, as the starting compound (XVI) in the second reaction, a fluoroolefin structurally different from the starting compound (IV) in the first reaction.

The compound (III) wherein the substituent of $R^{10}$ structurally differs from the substituent of $R^{11}$ can be also obtained by terminating the reaction in the single step of the first reaction, namely by carrying out only the first reaction, to completely react the hydroxyl group of the starting compound (XIII), or by indistinguishably conducting the first and second reactions using the same fluoroolefin as the starting compound (XIV) in the first reaction and as the starting compound (XVI) in the second reaction to completely react the hydroxyl group of the starting compound (XIII).

In fact, it is difficult to carry out the reactions with complete distinction and the reaction product obtained as a mixture of compounds would pose no particular problem. The obtained compound (III) to be used as a refrigerating machine oil is preferably one having a high volume resistivity and a low hygroscopicity, more specifically having a hydroxyl value of 80 or less, preferably 50 or less, more preferably 30 or less.

The conditions of the first and second reactions can be basically the same. These reactions can be conducted in the presence or the absence of a solvent. The amount of the solvent used is 0.1 to 100 times, preferably 0.5 to 10 times, more preferably 1 to 5 times, the total amount by volume of the starting compounds used. Examples of usable solvents are aprotic polar solvents such as methyl ethyl ketone, acetone, DMF, DMSO, NMP, sulfolane, diglyme, triglyme, ether, THF, chloroform, dichloromethane, etc.

In these reactions, a basic catalyst can be used as a catalyst or as a scavenger for removing HF produced as a by-product. The basic catalyst is used in an amount of 0.001 to 10 equivalents, preferably 0.01 to 5 equivalents, more preferably 0.1 to 2 equivalents, based on any one of the starting compounds used. Examples of the basic catalyst are inorganic bases such as KOH, NaOH, $K_2CO_3$, $Na_2CO_3$, etc. and organic bases such as triethylamine, tributylamine, etc.

The reaction temperature for these reactions is $-10$ to $200°$ C., preferably 0 to $150°$ C., more preferably 10 to $100°$ C. The reaction pressure is 0 to 50 $kg/cm^2G$, preferably 0 to 20 $kg/cm^2G$, more preferably 0 to 10 $kg/cm^2G$. The reaction time is 30 minutes to 100 hours, preferably 2 to 50 hours.

The ratios of the starting compounds to be used in these reactions, i.e. a (XIV)/(XIII) equivalent ratio and (XVI/XV) equivalent ratio, are each 0.01–20, preferably 0.5–10, more preferably 0.5–3.

When the compound (III) wherein the substituent of $R^{10}$ is a hydrogen atom is prepared only by the first reaction, and when the compound (III) wherein the substituent of $R^{10}$ structurally differs from the substituent of $R^{11}$ is prepared by the first and second reactions, a (XIV)/(XIII) equivalent ratio is preferably 0.5 to 1. When the compound (III) wherein the substituent of $R^{10}$ is structurally identical with the substituent of $R^{11}$ is prepared, a (XIV)/(XIII) equivalent ratio is preferably 1 to 3, and it is desired that the reaction be completely terminated only by the first reaction.

In any of the reactions, the starting compounds can be simultaneously charged or can be supplied by adding dropwise one of the starting compounds to the other or by blowing one to the other. Yet the invention is not limited in this respect.

There is no specific limitation on the treatment method to be carried out after the reaction, i.e. on the method for the recovery of the compound (III) from the reaction mixture. The compound can be purified by conventional methods. Stated more specifically, the reaction mixture is quenched in a large quantity of water and extracted with a water-immiscible solvent (such as S-3, dichloromethane, chloroform, etc.). The extract is washed with an acid, an alkali, a saturated aqueous solution of sodium chloride or the like, and dried over anhydrous sodium sulfate or anhydrous magnesium sulfate. After filtration, the solvent is distilled off from the filtrate at reduced pressure, whereby the compound (III) can be recovered. When required, the obtained product can be purified by vacuum distillation, column chromatography or the like.

Present Compound of the Formula (IV)

The symbol m in the formula (IV) is an integer of 2 to 5, n and n' are each an integer of 1 to 30, and $1 \leq n+n' \leq 30$.

$R^{16}$ and $R^{17}$ in the formula (IV) are each a hydrogen atom or a partly or fully fluorinated, straight- or branched-chain alkyl, alkenyl or alkoxyalkyl group having 1 to 50 carbon atoms, preferably 1 to 35 carbon atoms, more preferably 2 to 26 carbon atoms (which may be partly halogenated with a halogen other than a fluorine and may have 1 to 3 OH groups in the structure) or a partly or fully fluorinated fluoropolyether group having 2 to 700 carbon atoms, preferably 3 to 300 carbon atoms, more preferably 5 to 150 carbon atoms (which may be partly halogenated with a halogen other than a fluorine, may have 1 to 3 unsaturated bonds in the structure and may have an ether bond or bonds in the side chain).

The term "partly or fully fluorinated" used herein refers to (i) substituents with a structure wherein the hydrogen atoms of the alkyl, alkenyl or alkoxyalkyl group are partly or all substituted by a fluorine atom or atoms or (ii) a fluoropolyether group containing at least one fluorine atom in the structure. The term "which may be partly halogenated with a halogen other than a fluorine" used herein refers to (i) substituents with a structure wherein the remaining hydrogen atom or atoms of the partly fluorinated alkyl, alkenyl or alkoxyalkyl group are partly or all substituted by a halogen atom or atoms other than a fluorine atom, or (ii) a fluoropolyether group containing at least one halogen atom other than a fluorine atom in the structure, and the term "which may have 1 to 3 unsaturated bonds in the structure" used herein refers to a structure wherein 1 to 3 hydrogen atoms are substituted by OH groups.

Examples of substituents represented by $R^{16}$ and $R^{17}$ are straight- or branched-chain fluoroalkyl groups or fluoroalkyl hydroxide groups having a saturated structure, straight- or branched-chain fluoroalkenyl groups or fluoroalkenyl hydroxide groups having an unsaturated structure, etc.

Among the compounds of the formula (IV), the compounds containing, as the substituents of $R^{16}$ and $R^{17}$ a fluoroalkyl group, a fluoroalkenyl group, a fluoroalkoxyalkyl group or a fluoropolyether group having a fluorine/carbon atomic ratio of at least 0.6, preferably at least 1, more preferably at least 1.5 are suitable for use as a refrigerating machine oil and as a lubricant for magnetic recording media.

Specific examples of substituents represented by $R^{16}$ and $R^{17}$ are given below. They are desirable because of their easy availability in commercial manufacture, and do not limit the present invention.

H—
$HCF_2CF_2$—
$HCClFCF_2$—
$HCF_2CClF$—
$CF_3CFHCF_2$—
$CF_3CF=CF$—
$CF_2=CFCF_2$—
$CH_3CF_2$—
$(CF_3)_2CHCF_2$—
$HOC(CF_3)_2$—
$Cl(CF_2CClF)_iCFHCClF$— (i=integer of 1–20)

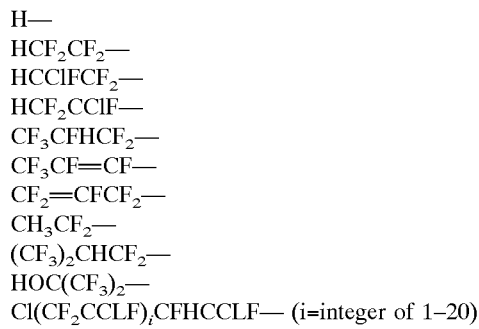

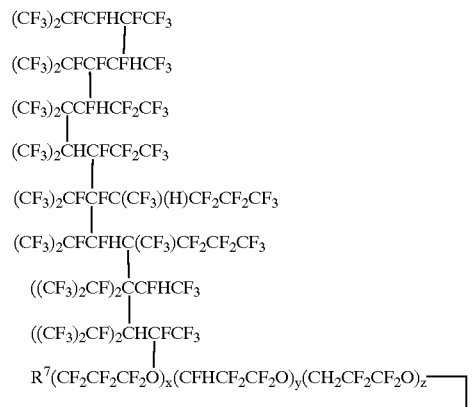

wherein x, y, z, v and w are each an integer of 0 to 100, provided that they can not be zero at the same time, and $R^7$ is a halogen atom or an alkoxy group having 1 to 3 carbon atoms (which may be partly or fully fluorinated), or $R^8(CF(CF_3)CF_2O)_p(CF_2CF_2O)_q(CF_2O)_rCFHCF_3$— wherein p, q and r are each an integer of 0 to 100, provided that they can not be zero at the same time, and $R^8$ is a halogen atom or an alkoxy group having 1 to 3 carbon atoms (which may be partly or fully fluorinated).

The fluoropolyether group represented by $R^{16}$ or $R^{17}$ can be formed, for example, using a fluoropolyether as the starting material (precursor) having, in the main chain structure, the corresponding perfluoropolyether, not fully fluorinated fluoropolyether or halogenated fluoropolyether partly substituted by a halogen atom or atoms other than a fluorine atom. Specific examples of fluoropolyethers usable as the starting material are shown below (manufacturers and trade names). These examples are desirable to use because they are commercial products and easily available. However, the invention is not limited to them.

"Demnam" (product of Daikin Industries Ltd.)

"Krytox" (product of E.I. du Pont de Nemours & Co., Inc.)

"Fomblin Y" (product of Montefluos Co., Ltd.)

"Fomblin Z" (product of Montefluos Co., Ltd.)

"Fomblin K" (product of Montefluos Co., Ltd.)

"Barierta" (product of NOK Kluva Co., Ltd.) $R^{19}$ and $R^{18}$ represent the same groups as those of $R^{16}$ and $R^{17}$ except that a hydrogen atom is present in the latter group, but not in the former.

Process for Preparing the Compound (IV)

The compound (IV) of the invention can be prepared by various processes, typically by a 4-step reaction represented by the following reaction formula (G).

Reaction Formula (G)

First Reaction

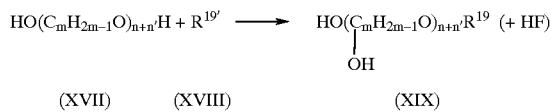

Second Reaction

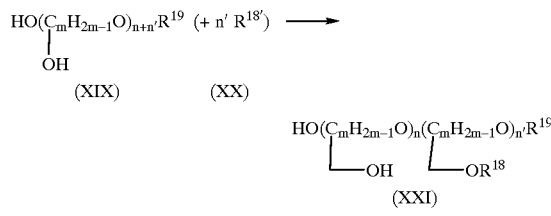

Third Reaction

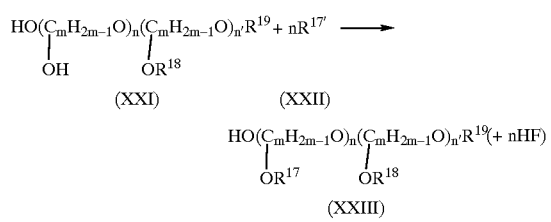

Fourth Reaction

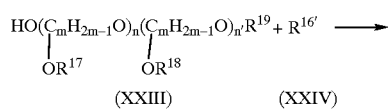

-continued

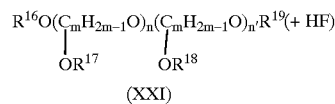

In the reaction formula (G), m is an integer of 2 to 5, n and n' are each an integer of 1 to 30, and $1 \leq n+n' \leq 30$. $R^{16}$, $R^{17}$, $R^{18}$ and $R^{19}$ are as defined above.

Given below are fluoroolefins and fluoroketones useful as the starting compounds (XXIV), (XXII), (XX) and (XVIII) represented by $R^{16'}$, $R^{17'}$, $R^{18'}$ and $R^{19'}$, respectively.

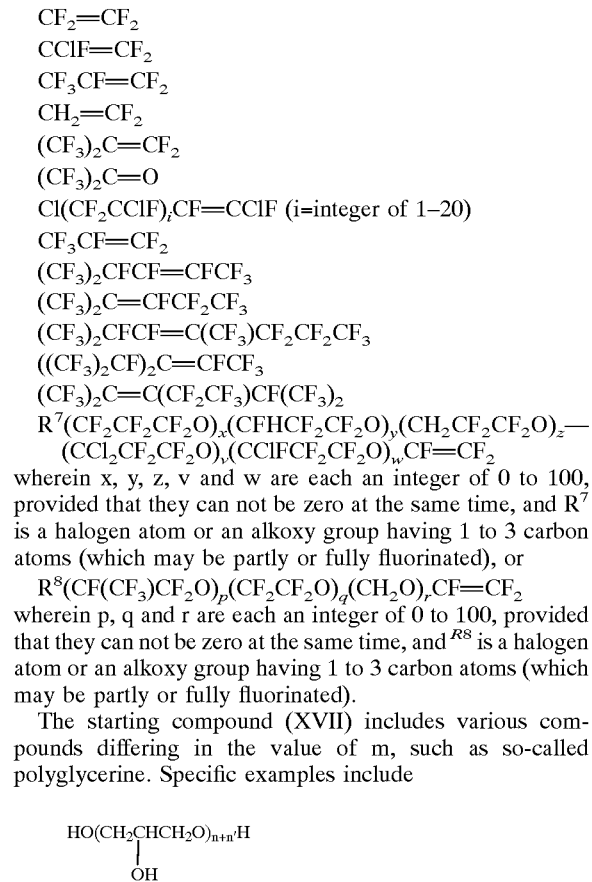

wherein x, y, z, v and w are each an integer of 0 to 100, provided that they can not be zero at the same time, and $R^7$ is a halogen atom or an alkoxy group having 1 to 3 carbon atoms (which may be partly or fully fluorinated), or $R^8(CF(CF_3)CF_2O)_p(CF_2CF_2O)_q(CH_2O)_rCF=CF_2$ wherein p, q and r are each an integer of 0 to 100, provided that they can not be zero at the same time, and $R^8$ is a halogen atom or an alkoxy group having 1 to 3 carbon atoms (which may be partly or fully fluorinated).

The starting compound (XVII) includes various compounds differing in the value of m, such as so-called polyglycerine. Specific examples include

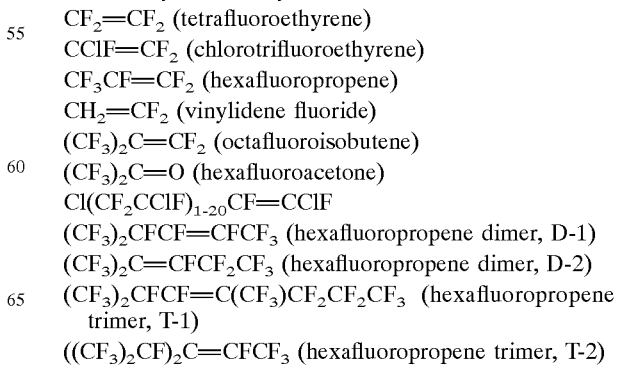

Numerous compounds are available as the starting compounds (VIII), (XX), (XXII) and (XXIV) as exemplified hereinbefore. Their typical examples are shown below. These fluoroolefins and fluoroketones are preferred in view of their ready availability but do not limit the invention.

$CF_2=CF_2$ (tetrafluoroethyrene)

$CClF=CF_2$ (chlorotrifluoroethyrene)

$CF_3CF=CF_2$ (hexafluoropropene)

$CH_2=CF_2$ (vinylidene fluoride)

$(CF_3)_2C=CF_2$ (octafluoroisobutene)

$(CF_3)_2C=O$ (hexafluoroacetone)

$Cl(CF_2CClF)_{1-20}CF=CClF$ $(CF_3)_2CFCF=CFCF_3$ (hexafluoropropene dimer, D-1)

$(CF_3)_2C=CFCF_2CF_3$ (hexafluoropropene dimer, D-2)

$(CF_3)_2CFCF=C(CF_3)CF_2CF_2CF_3$ (hexafluoropropene trimer, T-1)

$((CF_3)_2CF)_2C=CFCF_3$ (hexafluoropropene trimer, T-2)

$C_3F_7OCF=CF_2$
$C_3F_7OCF(CF_3)CF_2OCF=CF_2$
$C_3F_7O(CF(CF_3)CF_2O)_2CF=CF_2$

When the ratios of the starting compounds to be used in the second and third reactions subsequent to the first reaction, namely a (XX)/(XIX) equivalent ratio and (XXI)/(XXII) equivalent ratio, are each less than 1, or when the reaction time is shortened to terminate the reaction before its complete cease, compounds (XXI) and (XXIII) can be prepared wherein $R^{16}$, $R^{17}$ and $R^{18}$ of compound (IV) are each a hydrogen atom. When the reactions are carried out using different fluoroolefins as the starting compounds (XVIII), (XX), (XXII) and (XXIV), the compound (IV) can be prepared wherein the substituents of $R^{16}$, $R^{17}$ and $R^{18}$ are structurally different from each other.

The compound (IV) wherein the substituents of $R^{16}$, $R^{17}$, $R^{18}$ and $R^{19}$ are structurally identical with each other can be prepared by indistinguishably performing each step in the reactions using the same fluoroolefin as the starting compounds (XVIII), (XX), (XXII) and (XXIV) to completely react the hydroxyl group of the starting compound (XVIII). In fact, difficulty is entailed in conducting the reactions in completely separated steps, and the reaction product obtained as a mixture of compounds would pose no particular problem. The obtained compound to be used as a refrigerating machine oil is preferably one having a high volume resistivity and a low hygroscopicity, more specifically having a hydroxyl value of 80 or less, preferably 50 or less, more preferably 30 or less.

The first, second, third and fourth reactions can be performed basically under the same conditions. These reactions can be performed in the presence or the absence of a solvent. The amount of the solvent used is 0.1 to 100 times, preferably 0.5 to 10 times, more preferably 1 to 5 times, the total amount by volume of the starting compounds used. Examples of usable solvents are aprotic polar solvents such as methyl ethyl ketone, acetone, DMF, DMSO, NMP, sulfolane, diglyme, triglyme, ether, THF, chloroform, dichloromethane, etc.

In these reactions, a basic catalyst can be used as a catalyst or as a scavenger for removing HF produced as a by-product. The basic catalyst is used in an amount of 0.001 to 10 equivalents, preferably 0.01 to 5 equivalents, more preferably 0.1 to 2 equivalents, based on any one of the starting compounds used. Examples of the basic catalyst are inorganic bases such as KOH, NaOH, $K_2CO_3$, $Na_2CO_3$, etc. and organic bases such as triethylamine, tributylamine, etc.

The reaction temperature for these, reactions is -10 to 200° C., preferably 0 to 150° C., more preferably 10 to 100° C. The reaction pressure is 0 to 50 kg/cm²G, preferably 0 to 20 kg/cm²G, more preferably 0 to 10 kg/cm²G. The reaction time is 30 minutes to 100 hours, preferably 2 to 50 hours.

The ratios of the compounds to be used as the starting materials in these reactions, namely a (XVIII)/(XVII) equivalent ratio, (XX)/(XIX) equivalent ratio, (XXII)/(XXI) equivalent ratio, and (XIV)/(XXIII) equivalent ratio, are each 0.01–20, preferably 0.5–10, more preferably 0.5–3. When the compound (III) is prepared wherein the substituents of $R^{16}$, $R^{17}$ and $R^{18}$ are each a hydrogen atom, and when the compound (III) wherein the substituents of $R^{16}$, $R^{17}$ $R^{18}$ and $R^{19}$ structurally differ from each other is prepared by conducting the first, second, third and fourth reactions, a (XVIII)/(XVII) equivalent ratio, (XX)/(XIX) equivalent ratio, and (XXII)/(XXI) equivalent ratio are preferably each 0.5–1. When the compound (III) are prepared wherein the substituents of $R^{16}$, $R^{17}$ $R^{18}$ and $R^{19}$ are structurally identical with each other, a (XVIII)/(XVII) equivalent ratio, (XX)/(XIX) equivalent ratio, and (XXII)/(XXI) equivalent ratio are preferably each 1–3 and it is desired to completely terminate the reaction by effecting the first reaction alone.

In any case, the starting compounds can be simultaneously charged or can be supplied by adding dropwise one of the starting compounds to the other or by blowing one to the other. Yet the invention is not limited in this respect.

There is no specific limitation on the method for the recovery of the compound from the reaction mixture. The compound can be purified by conventional methods. Stated more specifically, the reaction mixture is quenched in a large quantity of water and extracted with a water-immiscible solvent (such as S-3, dichloromethane, chloroform, etc.). The extract is washed with an acid, an alkali, a saturated aqueous solution of sodium chloride or the like, and dried over anhydrous sodium sulfate or anhydrous magnesium sulfate. After filtration, the solvent is distilled off from the filtrate, whereby the compound (IV) can be recovered. When required, the obtained product can be purified by vacuum distillation, column chromatography or the like.

Present Compound of the Formula (V) and Process for its Preparation $R^{16}$, $R^{17}$ $R^{18}$ and $R^{19}$ in the formula (V) are as defined above for the formula (IV). That is, the compound (V) is the same as the compound (IV) except that in the compound (V), the basic skeleton of repeating units constituting the main chain is a polyglycerine structure represented by

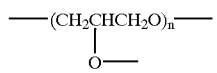

The compound (V) can be prepared in the same manner as the compound (IV) except that a polyglycerine having repeating units represented by

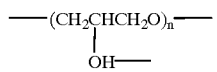

is used as the material for forming the main chain.

Use of Present Compounds

The compounds of the invention are excellent as an oil (refrigerator oil) for refrigerating machines which use as a refrigerant a hydrogen-containing halogenated hydrocarbon. The hydrogen-containing halogenated hydrocarbons referred to herein are not specifically limited and include, for example, hydrogen-containing fluorinated hydrocarbon (HFC), hydrogen-containing chlorinated fluorinated hydrocarbon (HCFC), etc. They are used singly or in mixture with each other. The abbreviation HFC used herein stands for a chlorine-free hydrogen-containing fluorinated hydrocarbon.

Specific examples of HFC are given below.

$CHF_3$ (HFC23)
$CH_2F_2$ (HFC32)
$CH_3F$ (HFC41)
$CHF_2CF_3$ (HFC125)
$CHF_2CHF_2$ (HFC134)
$CF_3CH_2F$ (HFC134a)
$CHF_2CH_2F$ (HFC143)
$CF_3CH_3$ (HFC143a)
$CH_2FCH_2F$ (HFC152)
$CHF_2CH_3$ (HFC152a)
$CH_2FCH_3$ (HFC161)
$CHF_2CF_2CF_3$ (HFC227ca)

CH$_2$FCF$_2$CF$_3$ (HFC236cb)
CH$_3$CF$_2$CF$_3$ (HFC245cb)
CH$_3$CF$_2$CHF$_2$ (HFC254cb)
CH$_3$CH$_2$CF$_3$ (HFC263fb)
CF$_3$CHFCF$_3$ (HFC227ea)

The compounds of the present invention are suitable for use as an oil for refrigerating machines using, among the above refrigerant examples, HFC23, HFC32, HFC125, HFC134a, HFC143a, HFC152a, HFC227ca, HFC227ea, etc. HFC's can be used singly or in mixture. Exemplified below are mixtures of two or more of HFC's.

Mixtures of two HFC's
HFC32/HFC134a
HFC125/HFC134a
HFC125/HFC143a

Mixtures of three HFC's
HFC32/HFC125/HFC134a
HFC23/HFC32/HFC134a
HFC125/HFC143a/HFC134a
HFC32/HFC125/HFC143a Specific examples of HCFC's are shown below.
CHClF$_2$ (HCFC22)
CHCl$_2$CF$_3$ (HCFC123)
CHClFCClF$_2$ (HCFC123a)
CHF$_2$CCl$_2$F (HCFC123b)
CHlFCF$_3$ (HCFC124)
CHF$_2$CClF$_2$ (HCFC124a)
CHClFCHF$_2$ (HCFC133)
CH$_2$ClCF$_3$ (HCFC133a)
CClF$_2$CH$_2$F (HCFC133b)
CHCl$_2$CH$_2$F (HCFC141a)
CCl$_2$FCH$_3$ (HCFC141b)
CHF$_2$CH$_2$Cl (HCFC142)
CHClFCH$_2$F (HCFC142a)
CClF$_2$CH$_3$ (HCFC142b)
CHClFCF$_2$CF$_3$ (HCFC226ca)
CH$_2$ClCF$_2$CF$_3$ (HCFC235cb)
CH$_3$CF$_2$CClF$_2$ (HCFC244cc)
CH$_3$CHClCF$_3$ (HCFC253db)
CH$_3$CH$_2$CClF$_2$ (HCFC262fc)

When HCFC22, HCFC124, HCFC123, HCFC141b, HCFC142b or HCFC235cb among said examples are used as a refrigerant in refrigerating machines, the compounds of the present invention are especially suitable for use in said machine. HCFC's can be used singly or in mixture.

When a mixture of HFC and HCFC is used, the component proportions are not specifically limited and may be selected from a proportion range in which the refrigerating machine can exhibit its highest capability.

For use as a refrigerator oil, the compound of the invention may be mixed with conventional refrigerator oils which do not adversely affect the capability of the compound of the invention as the refrigerator oil. Use of such mixture can reduce the cost of refrigerator oils and renders the substrate more wettable. If mixed in suitable proportions, these oils immiscible with each other can be unexpectedly emulsified to form a markedly stable, homogeneous layer over a wide temperature range. In view of this advantage, the mixture can display the desirable capability of refrigerator oil when used in combination with a specific refrigerant. Examples of conventional refrigerator oils which can be used are mineral oils, such as paraffin oils, naphthene oils, etc., alkylbenzenes, polybutenes, α-olefin oligomers, polyalkylene glycols, diesters, polyol esters, phosphoric esters, esters of silicic acid, silicones, polyphenyl ethers, etc.

Effects of the Invention

Because of high compatibility with hydrogen-containing halogenated hydrocarbons, the compound of the present invention is suitable for use as an oil for refrigerating machines using a hydrogen-containing halogenated hydrocarbon as a refrigerant. When employed in refrigerators together with a hydrogen-containing halogenated hydrocarbon (refrigerant), the compound of the invention is comparable or superior in the refrigerator capacity and coefficient of performance to conventional combinations of R-12 and mineral oil-based refrigerator oils.

Further the compound of the present invention shows a high durability, corrosion resistance and abrasion resistance as a lubricant for magnetic recording media.

EXAMPLE

Examples and Comparative Examples are given below to clarify the invention in further detail.

[Preparation of Refrigerating Machine Oil (Fluorine-containing Oil)]

Example 1

(Perfluorononenylphenyl ether)

A reactor was charged with 800 g (1.78 mol) of 6F trimer, 139 g (1.48 mol) of phenol and 500 g of DMF (dimethylformamide). A solution of 150 g (1.48 mol) of triethylamine in 100 g of DMF was added dropwise over a period of 30 minutes while the reaction mixture was kept at a temperature of 25° C. or lower. After completion of the addition, the reaction was allowed to proceed at 25° C. for 2.5 hours.

After completion of the reaction, the resultant reaction mixture was added dropwise to a 1N diluted hydrochloric acid and subjected to liquid separation. The lower layer (oil layer) was washed with 500 ml of water three times and dried over magnesium sulfate overnight. The crude product thus obtained was subjected to vacuum distillation to provide 550 g (yield: 71%) of the objective compound having a boiling point of 52.5–53.5° C./2 mmHg.

The compound thus obtained is represented by the following structural formula 1:

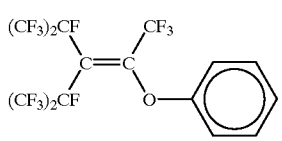

The structure of the compound was confirmed by $^1$H-NMR, $^{19}$F-NMR and GC-MS analyses.

The starting compound 6F trimer was synthesized by the method described in the literature "Nobuo Ishikawa, Akira Sekiya, Nippon Kagaku Kaishi, 1972, 2214".

Example 2

(p-Perfluorononenyloxybenzyl chloride)

A reactor was charged with 150 g (0.29 mol) of perfluorononenylphenyl ether and 34.6 g (0.43 mol) of chloromethylmethyl ether. While the mixture was cooled to 15° C. or lower, 18.3 g (0.23 mol) of fuming sulfuric acid ($SO_3$ content: 30%) was added dropwise over a period of 30 minutes. After completion of the addition, the reaction was allowed to proceed at 15° C. for 5 hours.

After completion of the reaction, the resultant reaction mixture was poured into water and the insoluble liquid was isolated. The crude product thus obtained was subjected to vacuum distillation to provide 117 g (yield: 71%) of the objective compound having a boiling point of 86.5–87.0° C./1.3 mmHg.

The compound thus obtained is represented by the following structural formula 2:

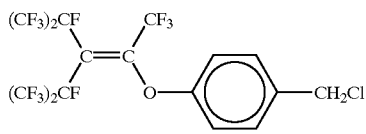

The structure of the compound was confirmed by $^1$H-NMR, $^{19}$F-NMR and GC-MS analyses.

Example 3

(Ethyl p-perfluorononenyloxybenzylphosphonate)

A reactor was charged with 10 g (17.5 mmol) of p-perfluorononenyloxybenzyl chloride and 3.5 g (21 mmol) of triethyl phosphate. The reaction was allowed to proceed with stirring at 150° C. for 30 hours. The completion of the reaction was confirmed by peak disappearance of the starting compound in gas chromatography.

After completion of the reaction, the resultant reaction mixture was poured into water and the insoluble liquid was isolated to provide 9.9 g (yield: 84%) of the objective compound.

The compound thus obtained is represented by the following structural formula 3:

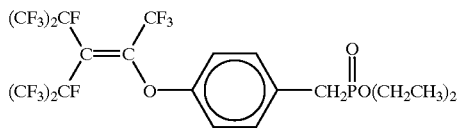

The structure of the compound was confirmed by $^1$H-NMR, $^{19}$F-NMR and GC-MS analyses.

Example 4

(Fluorine-containing Cyclic Compound)

A reactor was charged with 450 g (0.17 mol) of 6F trimer synthesized in the same manner as in Example 1. A solution of 25 g (0.25 mol) of triethylamine and 17 g (0.27 mol) of ethylene glycol in 50 ml of acetonitrile was added dropwise over a period of 30 minutes while the reaction mixture was kept at a temperature of 5° C. or lower. After completion of the addition, the reaction was allowed to proceed at 25° C. for 4 hours.

After completion of the reaction, the resultant reaction mixture was added dropwise to a 1N diluted hydrochloric acid and subjected to liquid separation. The lower layer (oil layer) was washed with 200 ml of water three times and dried over magnesium sulfate overnight. The crude product thus obtained was subjected to vacuum distillation to provide 51 g (yield: 64%) of the objective compound.

The compound thus obtained is represented by the following structural formula 4:

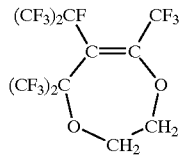

The structure of the compound was confirmed by $^1$H-NMR, $^{19}$F-NMR and GC-MS analyses.

[Solubility Test of Refrigerants]

Examples 5–12 and Comparative Examples 1–5

The solution temperature range of mixed refrigerants and refrigerating machine oils was determined using the mixed refrigerants and refrigerating machine oils shown in Table 1. The HFC134a/HFC32 mixed refrigerant was in the ratio 70:30 (by weight). The HFC125/HFC32 mixed refrigerant was in the ratio 40:60 (by weight).

The solution temperature range was determined as follows. The refrigerating machine oils (0.3–0.5 g), i.e. those prepared in Examples 1–4 or commercially available refrigerating machine oils A–C and the mixed refrigerants (1.2–2.0 g) shown in Table 1 were vacuum sealed in a glass pressure tube in the oil-refrigerant ratio by weight of 1:4. The tube was cooled or heated and the dissolved state of the oils and the refrigerants was visually inspected to determine the lower limit (low temperature) and upper limit (high temperature) of the temperature at which they became compatible.

TABLE 1

| | Refrigerant | Refrigerating machine oil | Solution temperature range (° C.) | |
| --- | --- | --- | --- | --- |
| | | | The lower limit | The upper limit |
| Ex. 5 | HFC134a HFC32 | oil in Example 1 | −40 | Critical temperature |
| Ex. 6 | HFC125 HFC32 | oil in Example 1 | −40 | Critical temperature |
| Ex. 7 | HFC134a HFC32 | oil in Example 2 | −40 | Critical temperature |
| Ex. 8 | HFC125 HFC32 | oil in Example 2 | −40 | Critical temperature |
| Ex. 9 | HFC134a HFC32 | oil in Example 3 | −40 | Critical temperature |
| Ex. 10 | HFC125 HFC32 | oil in Example 3 | −40 | Critical temperature |
| Ex. 11 | HFC134a HFC32 | oil in Example 4 | −40 | Critical temperature |
| Ex. 12 | HFC125 HFC32 | oil in Example 4 | −40 | Critical temperature |
| Com. Ex.1 | HFC134a HFC32 | oil A | Insoluble | |
| Com. Ex.2 | HFC125 HFC32 | oil A | Insoluble | |
| Com. Ex.3 | HFC134a HFC32 | oil B | −10 | Critical temperature |
| Com. Ex.4 | HFC125 HFC32 | oil B | −10 | 75 |
| Com. Ex.5 | HFC134a HFC32 | oil C | −20 | 80 |
| Com. Ex.6 | HFC125 HFC32 | oil C | −20 | 50 |

The refrigerating machine oils A, B and C in Table 1 represent naphthenic mineral oil "Suniso 4GS®" (Nippon Sun Oil Co., Ltd.), "Konidine DS-401®" (Daikin Industrial Co., Ltd.) and "Konidine DS-406®" (Daikin Industrial Co., Ltd.) respectively.

Processes for Preparing Lubricants (Fluorinated Hydrocarbon Compounds) of the Invention The processes for preparing lubricants according to the invention can be roughly divided into two types depending on the fluorine-containing compound and hydrocarbon compound to be used as the starting compounds, namely on which compound has nucleophilicity.

Compounds having nucleophilicity include alcohols and amines. Fluorine-containing compounds having nucleophilicity include the compounds of formula 1: R—CH$_2$OH wherein R— represents CF$_3$—, CF$_3$CF$_2$(CF$_2$CF$_2$)$_n$—,

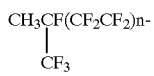

or H(CF$_2$CF$_2$)$_m$— wherein n represents an integer of 0–10, m represents an integer of 1–10, and the compounds of the formula 2: R—CH$_2$NH$_2$ wherein R— represents CF$_3$—, CF$_3$CF$_2$(CF$_2$CF$_2$)$_n$—,

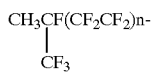

or H(CF$_2$CF$_2$)m—
wherein n represents an integer of 0–10 and m represents an integer of 1–10. Hydrocarbon compounds having nucleophilicity include the compounds of formula 3: R—CH$_2$OH wherein R— represents H—, a C$_{1-20}$ alkyl group or a C$_{6-50}$ aromatic group, and the compounds of formula 4: R—CH$_2$NH$_2$ wherein R— represents H—, a C$_{1-20}$ alkyl group or a C$_{6-50}$ aromatic group. Suitably used as the fluorine-containing alcohol is R(CF$_2$)$_n$(CH$_2$)$_n$—OH wherein R represents H or F and n represents an integer of 1–10.

When a fluorine-containing compound of nucleophilicity is used, a hydrocarbon compound receptive to nucleophilic reaction is used. On the other hand, when a hydrocarbon compound of nucleophilicity is used, a fluorine-containing compound receptive to nucleophilic reaction is used.

Compounds receptive to nucleophilic reaction include olefins and epoxy compounds. Hydrocarbon compounds receptive to nucleophilic reaction include the compounds of formula 5:

wherein —A— represents

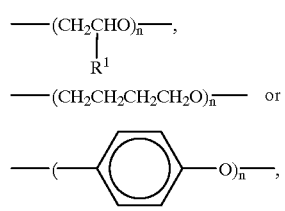

R— represents H—, a C$_{1-20}$ alkyl group or a C$_{6-50}$ aromatic group wherein n represents an integer of 1–1000 and R$^1$— represents H— or a C$_{1-12}$ alkyl group. Fluorine-containing compounds receptive to nucleophilic reaction include the compounds of formula 6:

wherein R— represents CF$_3$—, CF$_3$CF$_2$(CF$_2$CF$_2$)$_n$—,

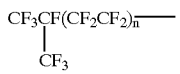

or H(CF$_2$CF$_2$)$_m$ — wherein n represents an integer of 0–10 and m represents an integer of 1–10. Perfluoroolefines are suitably used as fluorine-containing olefins. Among them, CF$_2$=CF$_2$, CF$_3$CF=CF$_2$, (CF$_3$)$_2$C=CF$_2$ or oligomers thereof are preferred and the dimer or trimer of CF$_3$CF=CF$_2$ is more preferred.

Whichever may be nucleophilic, the fluorine compound or hydrocarbon compound, a suitable hydrocarbon is one having an ether bond. Specific examples include the compounds having one of the following repeating units 1–5:
repeating unit 1

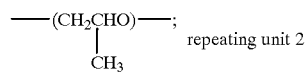

repeating unit 3

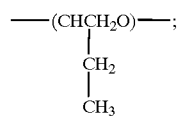 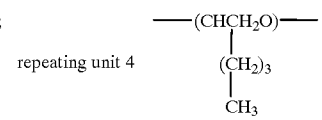

and repeating unit 5—(CH$_2$CH$_2$CH$_2$CH$_2$O)—.

According to the process of the present invention, the nucleophilic reaction can be either homogeneous or heterogeneous and either a gas phase or liquid phase reaction. In addition, the reaction is feasible with or without a solvent.

A reaction catalyst need not be used but may be used. It is preferred to use a reaction catalyst, for the increase of reactivity, e g. inorganic alkalis such as KOH and NaOH, organic alkalis such as triethylamine, Lewis acid catalysts such as BF$_3$OEt$_2$ (wherein Et represents an ethyl group) and AlCl$_3$ and the like. The reaction is carried out at a temperature of 0–200° C., preferably 40–140° C. In this case, the reaction time is 30 minutes to 48 hours, preferably 1–24 hours.

Specific examples of the nucleophilic reaction to be conducted in the process of the invention are given below which are represented by the following reaction formulas 1–12.

Reaction Formula 1

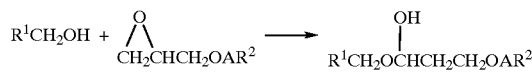

wherein $R^1$— represents $CF_3$—, $CF_3CF_2(CF_2CF_2)_n$—,

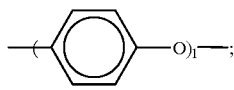 or $H(CF_2CF_2)_{\overline{m}}$—;

A represents —$(CH_2CHO)_l$—,
                    |
                    $R^3$

—$(CH_2CH_2CH_2CH_2O)_l$ or

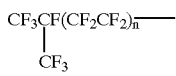

$R^2$— represents H—, a $C_{1-20}$ alkyl group or a $C_{6-50}$ aromatic group; n represents an integer of 0–10; m represents an integer of 1–10; l represents an integer of 1–1000; and $R^3$— represents H—, $CH_3$— or $CH_2CH_3$—.

Reaction Formula 2

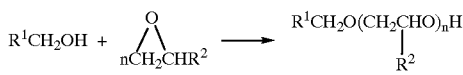

wherein $R^1$— represents $CF_3$, $CF_3CF_2(CF_2CF_2)_n$—, $CF_3CF(CF_2CF_2)_{\overline{n}}$—
  |
  $CF_3$ or $H(CF_2CF_2)_m$—; $R^2$— represents H—, $CH_3$— or $CH_2CH_3$—; and n represents an integer of 0–1000.

Reaction Formula 3

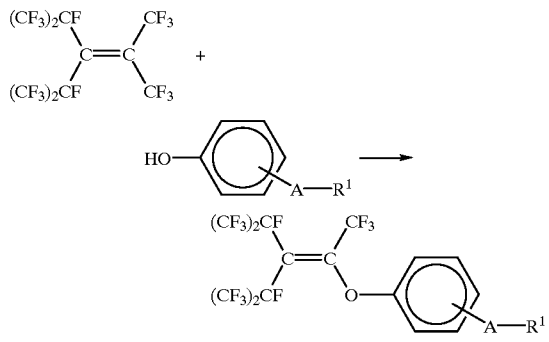

wherein A represents O, a $C_{1-20}$ alkylene group, a $C_{6-50}$ aromatic group,

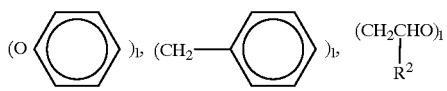

or $[(CH_2)_mO]$ wherein m represents an integer of 1–5, l represents an integer of 1–1000; and $R^2$ represents H or a $C_{1-5}$ alkyl group; and $R^1$ represents H, a $C_{1-20}$ alkyl group, Cl, Br, I,

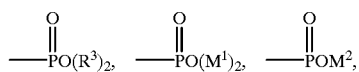

—OH or $F(CF_2CF_2CF_2O)_nCF_2CF_2CH_2$— wherein $R^3$ represents a $C_{1-20}$ alkyl group, $M^1$ represents a monovalent metal, $M^2$ represents a bivalent metal and n represents an integer of 1–100.

Reaction Formula 4

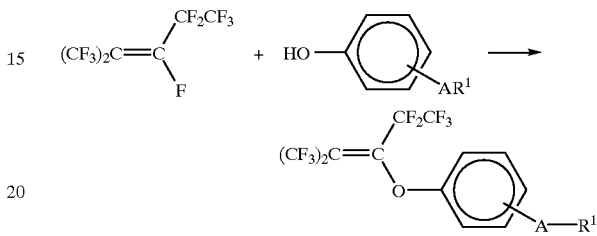

wherein A and $R^1$ represent the same as in reaction formula 4.

Reaction Formula 5

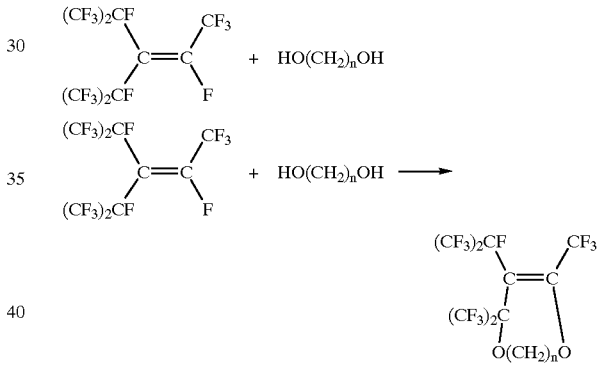

wherein n represents an integer of 1–100.

Reaction Formula 6

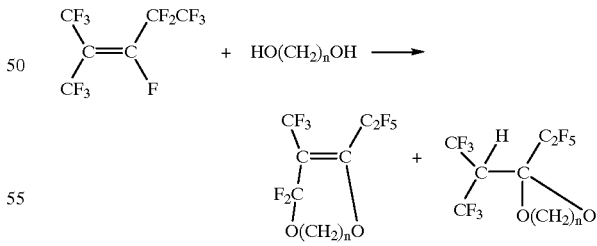

wherein n represents an integer of 1–100.

Reaction Formula 7

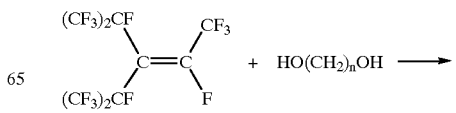

-continued

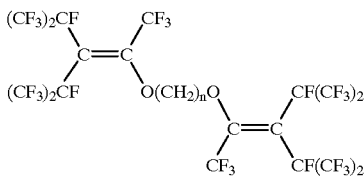

wherein n represents an integer of 1–100.

Reaction Formula 8

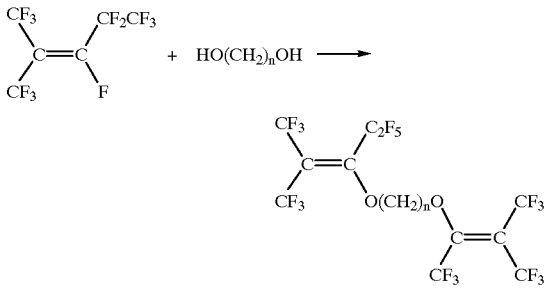

wherein n represents an integer of 1–100.

Reaction Formula 9

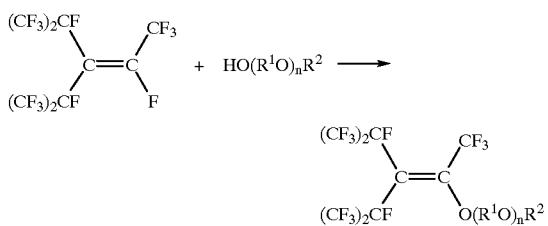

wherein $R^1$ represents

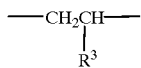

or —$CH_2CH_2CH_2CH_2O$— wherein $R^3$ represents H or a $C_{1-12}$ alkyl group; and $R^2$ represents H, a $C_{1-20}$ alkyl group, a $C_{6-50}$ aromatic group; and n represents an integer of 1–1000.

Reaction formula 10

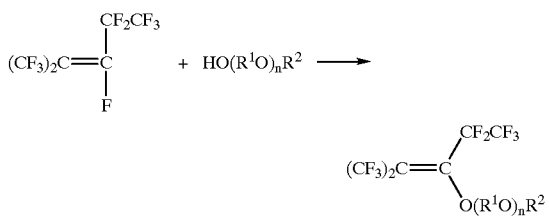

wherein $R^1$, $R^2$ and n represent the same as in reaction formula 9.

Reaction Formula 11

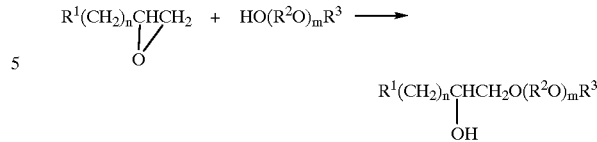

wherein $R^1$ represents the same as in reaction formula 3; $R^2$ represents

—$CH_2CH$—, $CH_2CH_2CH_2CH_2$— or ⌬—;
    |
    $R^3$ and $R^3$ represents H, a $C_{1-20}$ alkyl group or a $C_{6-50}$ aromatic group; n represents an integer of 0–6; and m represents an integer of 1–1000; and $R^4$ represents H or a $C_{1-12}$ alkyl group.

Reaction Formula 12

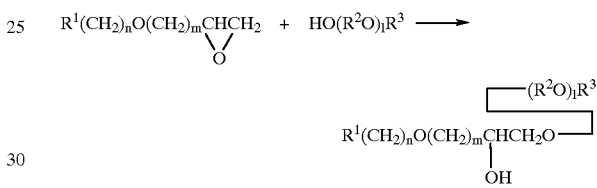

wherein $R^1$, $R^2$ and $R^3$ represent the same as in reaction formula 11; n represents an integer of 0–6; m represents an integer of 0–6; and l represents an integer of 1–1000.

The lubricant of the present invention comprises a fluorine-containing oil produced by subjecting said fluorine-containing compound and said hydrocarbon to nucleophilic reaction. Examples of such fluorine-containing oil include the reaction products prepared by the processes shown in reaction formulas 1–12. The lubricants of the invention are not specifically limited, but suitable lubricants are those having a number average molecular weight of 200–100000, preferably 300–20000.

Example 13

A 4-necked flask was charged with 6.8 g of stearyl alcohol, 9 g of $Et_3N$ and 100 cc of MEK. While the mixture was stirred at a predetermined temperature, 40 g of hexafluoropropylene trimer (T-1/T-2=35/65) was added dropwise. After completion of the reaction, the reaction mixture was extracted with S-3 and washed with a 1N aqueous HCl solution and a saturated aqueous NaCl solution. The organic layer was dried over $Na_2SO_4$, filtered and concentrated under reduced pressure at 50° C., giving 35.6 g of an oily compound (T-1 origin/T-2 origin=35/65).

Example 14

A 4-necked flask was charged with 20.8 g of isostearyl alcohol having an average molecular weight of 270, 8.9 g of $Et_3N$ and 100 cc of MEK. While the mixture was stirred at a predetermined temperature, 50 g of hexafluoropropylene trimer (T-1/T-2=35/65) was added dropwise. After completion of the reaction, the reaction mixture was extracted with S-3 and washed with a 1N aqueous HCl solution and a saturated aqueous NaCl solution. The organic layer was dried over $Na_2SO_4$, filtered and concentrated under reduced pressure at 50° C., giving 47.5 g of an oily compound (T-1 origin/T-2 origin=35/65).

Example 15

A 4-necked flask was charged with 20.8 g of isostearyl alcohol having an average molecular weight of 270, 8.9 g of $Et_3N$ and 100 cc of MEK. While the mixture was stirred at a predetermined temperature, 45 g of hexafluoropropylene trimer (T-1/T-2=15/85) was added dropwise. After completion of the reaction, the reaction mixture was extracted with S-3 and washed with a 1N aqueous HCl solution and a saturated aqueous NaCl solution. The organic layer was dried over $Na_2SO_4$, filtered and concentrated under reduced pressure at 50° C., giving 52 g of an oily compound (T-1 origin/T-2 origin=15/85).

Example 16

A 4-necked flask was charged with 12 g of polypropylene glycol having an average molecular weight of 1004, 3.3 g of $K_2CO_3$ and 60 cc of MEK. While the mixture was stirred at a predetermined temperature, 10 g of hexafluoropropylene trimer (T-1/T-2=35/65) was added dropwise. After completion of the reaction, the reaction mixture was extracted with S-3 and washed with a 1N aqueous HCl solution and a saturated aqueous NaCl solution. The organic layer was dried over $Na_2SO_4$, filtered and concentrated under reduced pressure at 50° C., giving 16 g of an oily compound.

Example 17

A 200 cc autoclave was charged with 10 g of pentaerythritol, 16.4 g of KOH and 80 cc of DMSO. After nitrogen substitution, 34.1 g of chlorotrifluoroethylene was added under reduced pressure. While chlorotrifluoroethylene was continuously fed for replenishment, the reaction proceeded correspondingly as the reaction temperature rose. After completion of the reaction, the reaction mixture was extracted with S-3 and washed with water, a 1N aqueous HCQ solution and a saturated aqueous NaCl solution. The organic layer was dried over $Na_2SO_4$, filtered and concentrated under reduced pressure at 50° C., giving 37 g of an oily compound.

Example 18

A 500 cc autoclave was charged with 50 g of pentaerythritol, 48 g of KOH and 150 cc of DMSO. After nitrogen substitution, 150 g of tetrafluoroethylene was added under reduced pressure. While tetrafluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 180 g of an oily compound.

Example 19

A 500 cc autoclave was charged with 30 g of trimethylolpropane, 44.3 g of KOH and 150 g of DMSO. After nitrogen substitution, 68 g of tetrafluoroethylene was added under reduced pressure. While tetrafluoroethylene was continuously supplied for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 95 g of an oily compound.

Example 20

A 500 cc autoclave was charged with 30 g of trimethylolethane, 49.3 g of KOH and 150 cc of DMSO. After nitrogen substitution, 75 g of tetrafluoroethylene was added under reduced pressure. While tetrafluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 100 g of an oily compound.

Example 21

A 500 cc autoclave was charged with 30 g of neopentyl glycol, 4.7 g of KOH and 200 cc of DMSO. After nitrogen substitution, 57.6 g of tetrafluoroethylene was added under reduced pressure. While tetrafluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 85.3 g of an oily compound.

Example 22

A 500 cc autoclave was charged with 30 g of neopentyl glycol, 9.5 g of KOH and 200 cc of DMSO. After nitrogen substitution, 67 g of chlorotrifluoroethylene was added under reduced pressure. While chlorotrifluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 96.3 g of an oily compound.

Example 23

A 500 cc autoclave was charged with 30 g of neopentyl alcohol, 2.2 g of KOH and 200 cc of DMSO. After nitrogen substitution, 40 g of chlorotrifluoroethylene was added under reduced pressure. While chlorotrifluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 66.3 g of an oily compound.

Example 24

A 500 cc autoclave was charged with 30 g of hexane diol, 1.6 g of KOH and 200 cc of DMSO. After nitrogen substitution, 59.2 g of chlorotrifluoroethylene was added under reduced pressure. While chlorotrifluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 85.8 g of an oily compound.

Example 25

A 500 cc autoclave was charged with 30 g of glycerin, 21.5 g of KOH and 200 cc of DMSO. After nitrogen substitution, 113.8 g of chlorotrifluoroethylene was added under reduced pressure. While chlorotrifluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 135 g of an oily compound.

Example 26

A 500 cc autoclave was charged with 30 g of neopentyl glycol, 4.7 g of KOH and 200 cc of DMSO. After nitrogen substitution, 86 g of hexafluoropropene was added under reduced pressure. While hexafluoropropene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 100.0 g of an oily compound.

Example 27

A 500 cc autoclave was charged with 30 g of pentaerythritol, 0.9 g of NaOH and 200 cc of DMSO. After nitrogen substitution, 132 g of hexafluoropropane was added under reduced pressure. While hexafluoropropane was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 150 g of an oily compound.

Example 28

A 500 cc autoclave was charged with 50 g of diglycerin, 5.8 g of KOH and 200 cc of DMSO. After nitrogen substitution, 140.2 g of chlorotrifluoroethylene was added under reduced pressure. While chlorotrifluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 175.6 g of an oily compound.

Example 29

A 500 cc autoclave was charged with 30 g of trimethylolpropane, 2 g of NaOH and 200 cc of DMSO. After nitrogen substitution, 78 g of chlorotrifluoroethane was added under reduced pressure. While chlorotrifluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 74 g of an oily compound.

Example 30

A 500 cc autoclave was charged with 30 g of trimethylolethane, 2.1 g of NaOH and 200 cc of DMSO. After nitrogen substitution, 96 g of chlorotrifluoroethylene was added under reduced pressure. While chlorotrifluoroethylene was continuously fed for replenishment, the reaction proceeded correspondingly as the reaction temperature rose. After completion of the reaction, the reaction mixture was extracted with S-3 and washed with water, a 1N aqueous HCl solution and a saturated aqueous NaCl solution. The organic layer was dried over $Na_2SO_4$, filtered and concentrated under reduced pressure at 50° C., giving 83 g of an oily compound.

Example 31

A solution of 50 g of perfluorooctyl ethanol in 50 cc triglyme and 4.5 cc of $BF_3OEt_2$ were placed in a flask and stirred at 50° C. Then 21 g of polypropylene glycol epoxy having an average molecular weight of 195.8 was dropwise added. After completion of the reaction, the reaction mixture was extracted with S-3 and washed with a saturated aqueous $NaHCO_3$ solution and a saturated aqueous NaCl solution. The organic layer was dried over $Na_2SO_4$, filtered and concentrated under reduced pressure at 50° C., giving 65.5 g of an oily compound.

Example 32

A 4-necked flask was charged with 10 g of glycerin, 40 g of $Et_3N$ and 150 cc of MEK. While the mixture was stirred at room temperature, 175 g of hexafluoropropylene trimer (T-1/T-2=35/65) was dropwise added. After completion of the reaction, the reaction mixture was extracted with S-3 and washed with a 1N aqueous HCl solution and a saturated aqueous NaCl solution. The organic layer was dried over $Na_2SO_4$, filtered and concentrated under reduced pressure at 50° C., giving 140.3 g of an oily compound (T-1 origin/T-2 origin=35/65).

Example 33

A 4-necked flask was charged with 26.85 g of oleyl alcohol and 1.5 ml of $BF_3OEt$. While the mixture was stirred at 75° C., 47.6 g of 3-perfluorooctyl-1,2-epoxypropane was dropwise added and then stirred at 80° C. After completion of the reaction, water was added and the reaction mixture was extracted with diethyl ether. The organic layer was dried over $MgSO_4$, filtered and concentrated under reduced pressure at 50° C., giving 70.5 g of an oily compound.

Example 34

A 4-necked flask was charged with 46.4 g of 3-perfluorooctyl-1-ethanol and 1.5 ml of $BF_3OEt$. While the mixture was stirred at 75° C., 18.5 g of epichlorhydrin was dropwise added and then stirred at 80° C. After completion of the reaction, water was added and the reaction mixture

Example 35

A 4-necked flask was charged with 46.4 g of 3-perfluorooctyl-1-ethanol and 1.5 ml of BF$_3$OEt. While the mixture was stirred at 75° C., 526 g of 3-perfluoro(7-methyloctyl)-1,2-epoxypropane was dropwise added and then stirred at 80° C. After completion of the reaction, water was added and the reaction mixture was extracted with diethyl ether. The organic layer was dried over MgSO$_4$, filtered and concentrated under reduced pressure at 50° C., giving 565 g of an oily compound.

Example 36

A 4-necked flask was charged with 46.4 g of 3-perfluorooctyl-1-ethanol and 1.5 ml of BF$_3$OEt. While the mixture was stirred at 75° C., 39 g of 3-n-buthyloxy-1,2-epoxypropane was dropwise added and then stirred at 80° C. After completion of the reaction, water was added and the reaction mixture was extracted with diethyl ether. The organic layer was dried over MgSO$_4$, filtered and concentrated under reduced pressure at 50° C., giving 79 g of an oily compound.

Example 37

A 4-necked flask was charged with 8.5 g of 2-chloro-1-ethanol and 1.5 ml of BF$_3$OEt. While the mixture was stirred at 75° C., 52.6 g of 3-perfluoro(7-methyloctyl)-1,2-epoxypropane was dropwise added and then stirred at 80° C. After completion of the reaction, water was added and the reaction mixture was extracted with diethyl ether. The organic layer was dried over MgSO$_4$, filtered and concentrated under reduced pressure at 50° C., giving 60 g of an oily compound.

Example 38

A 500-mL flask was charged with 100 g of isostearyl alcohol having the average molecular weight of 270, 100 mL of chloroform solvent and 0.5 mL of BF$_3$ etherate. While the mixture was heated at 60° C. and refluxed, 194.6 g (0.37 mol) of perfluoroepoxy compound (CF$_3$)$_2$CF(CF$_2$)$_6$CH$_2$C$_2$H$_3$O was slowly added dropwise through a dropping funnel. The heating and stirring were continued for 12 hours. After completion of the reaction, the reaction mixture was washed with a 10% NaHCO$_3$ solution and dried over anhydrous magnesium sulfate and the solvent in the filtrate was distilled off under reduced pressure, giving 281 g of a light yellow oily compound.

Example 39

A 500-mL flask was charged with 50 g of isomyristyl alcohol having the average molecular weight of 214, 100 mL of chloroform solvent and 0.5 mL of BF$_3$ etherate. While the mixture was heated at 60° C. and refluxed, 158.8 g (0.30 mol) of perfluoroepoxy compound (CF$_3$)$_2$CF(CF$_2$)$_6$CH$_2$C$_2$H$_3$O was slowly added dropwise through a dropping funnel. The heating and stirring were continued for 12 hours. After completion of the reaction, the reaction mixture was washed with a 10% NaHCO$_3$ solution and dried over anhydrous magnesium sulfate and the solvent in the filtrate was distilled off under reduced pressure, giving 207.7 g of a colorless oily compound.

Example 40

A 500-mL SUS 316 autoclave was charged with 56.2 g of polyglycelin (OH value 1045 mg/g), 300 mL of dimethyl sulfoxide and 10.0 g of KOH. While the mixture was stirred at room temperature, tetrafluoroethylene (hereinafter briefly referred to as TFE) was added to the liquid phase at a pressure of 5 kg/cm$^2$·G. The exothermic reaction increased the reaction temperature to 50° C.

After stirring for 2.5 hours, unreacted TFE was purged and 100 mL of chloroform was added. The reaction mixture was washed with a 5% aqueous HCl solution and a 10% NaHCO$_3$ solution, dried over anhydrous magnesium sulfate and filtered. The solvent in the filtrate was distilled off under reduced pressure, giving 113.2 g of a colorless oily compound.

Example 41

A 500-mL SUS 316 autoclave was charged with 57.2 g of polyglycelin (OH value 969 mg/g), 300 mL of dimethyl sulfoxide and 10.3 g of KOH. While the mixture was stirred at room temperature, TFE was added to the liquid phase at a pressure of 5 kg/cm$^2$·G. The exothermic reaction increased the reaction temperature to 52° C.

After stirring for 6 hours, unreacted TFE was purged and 100 mL of chloroform was added. The reaction mixture was washed with a 5% aqueous HCl solution and water, dried over anhydrous magnesium sulfate and filtered. The solvent in the filtrate was distilled off under reduced pressure, giving 124.7 g of a colorless oily compound.

Example 42

A 500-mL SUS 316 autoclave was charged with 49.7 g of polyglycelin (OH value 1045 mg/g), 300 mL of acetonitrile and 10.0 g of 50% KOH. While the mixture was stirred at room temperature, chlorotrifluoroethylene (hereinafter briefly referred to as CTFE) was added to the liquid phase at a pressure of 4 kg/cm$^2$·G.

After stirring for 6 hours, unreacted CTFE was purged and 100 mL of chloroform was added. The reaction mixture was washed with a 5% aqueous HCl solution and a 10% NaHCO$_3$ solution, dried over anhydrous magnesium sulfate and filtered. The solvent in the filtrate was distilled off under reduced pressure, giving 103.4 g of a colorless oily compound.

Example 43

A 500-mL SUS 316 autoclave was charged with 50.1 g of polyglycelin (OH value 1045 mg/g), 300 mL of dimethyl sulfoxide and 10.5 g of KOH. While the mixture was stirred at room temperature, CTFE was added to the liquid phase at a pressure of 4 kg/cm$^2$·G.

After stirring for 4 hours, unreacted CTFE was purged and 100 mL of chloroform was added. The reaction mixture was washed with a 5% aqueous HCl solution and a 10% NaHCO$_3$ solution, dried over anhydrous magnesium sulfate and filtered. The solvent in the filtrate was distilled off under reduced pressure, giving 136.9 g of a yellow oily compound.

Example 44

A 500-mL SUS 316 autoclave was charged with 50.7 g of polyglycelin (OH value 969 mg/g), 300 mL of dimethyl sulfoxide and 10.2 g of KOH. While the mixture was stirred at room temperature, CTFE was added to the liquid phase at a pressure of 4 kg/cm$^2$·G.

After stirring for 4 hours, unreacted CTFE was purged and 100 mL of chloroform was added. The reaction mixture was washed with a 5% aqueous HCl solution and a 10%

NaHCO$_3$ solution, dried over anhydrous magnesium sulfate and filtered. The solvent in the filtrate was distilled off under reduced pressure, giving 115.4 g of a brown oily compound.

Example 45

A 500-mL SUS 316 autoclave was charged with 57.8 g of polyglycelin (OH value 882 mg/g), 300 mL of dimethyl sulfoxide and 10.5 g of KOH. While the mixture was stirred at room temperature, TFE was added to the liquid phase at a pressure of 4 kg/cm$^2$·G.

After stirring for 4 hours, unreacted TFE was purged and 100 mL of chloroform was added. The reaction mixture was washed with a 5% aqueous HCl solution and a 10% NaHCO$_3$ solution, dried over anhydrous magnesium sulfate and filtered. The solvent in the filtrate was distilled off under reduced pressure, giving 100.9 g of a brown oily compound.

Example 46

A 500-mL SUS 316 autoclave was charged with 55.4 g of diglycelin, 300 mL of dimethyl sulfoxide and 10.0 g of KOH. While the mixture was stirred at room temperature, TFE was added to the liquid phase at a pressure of 4 kg/cm$^2$·G.

After stirring for 10 hours, unreacted TFE was purged and 100 mL of chloroform was added. The reaction mixture was washed with a 5% aqueous HCl solution and a 10% NaHCO$_3$ solution, dried over anhydrous magnesium sulfate and filtered. The solvent in the filtrate was distilled off under reduced pressure, giving 138.0 g of a yellow oily compound.

Example 47

A 500-mL flask was charged with 100.8 g of hexafluoropropylene dimer (perfluorohexene D-1: 94%; D-2: 6%), 82.8 g of isoicosyl alcohol having the average molecular weight of 298 and 300 mL of methylethyl ketone. While the mixture was stirred at room temperature, 29.3 g of triethylamine was added dropwise.

After stirring for 2 days, the reaction mixture was washed with a 5% aqueous HCl solution, a 10% NaHCO$_3$ solution and saturated aqueous NaCl solution, dried over anhydrous magnesium sulfate and filtered. The solvent in the filtrate was distilled off under reduced pressure, giving 119.5 g of a brown oily compound.

Example 48

A 50-mL flask was charged with 20.0 g of isopalmityl alcohol having an average molecular weight of 249. While the alcohol was stirred at room temperature, 20 g of hexafluoroacetone was slowly blown into the flask. In two hours, unreacted gas was distilled off under reduced pressure, giving 33.1 g of a yellow oily compound.

Example 49

In a 4-necked flask, 59.1 g of 1,6-hexanediol was dissolved in 600 cc of CH$_3$CN and K$_2$CO$_3$ was added. Then 300 g of hexafluoropropylene dimer (perfluorohexene D-1: 94%; D-2: 6%) was dropwise added at 5–10° C. and stirred for 18 hours. After completion of the reaction, the reaction mixture was filtered and washed with water five times. The organic layer was separated, dried over anhydrous magnesium sulfate and filtered, giving 461 g of an oily compound.

Example 50

In a 4-necked flask, 200 g of polypropylene glycol having an average molecular weight of 1055 was dissolved in 200 cc of CH$_2$Cl$_2$ and 0.03 ml of BF$_3$OEt was added. Then 150 g of isoperfluorooctylpropoxy which had been heated and refluxed was dropwise added. After completion of the reaction, the reaction mixture was extracted with CH$_2$Cl$_2$ and washed with saturated NaHCO$_3$ and pure water. The organic layer was separated, dried over Na$_2$SO$_4$, filtered and concentrated under reduced pressure at 50° C., giving 280 g of an oily compound.

Example 51

In a 4-necked flask, 60 g of the epoxy compound $$H(CF_2CF_2)_3CH_2OCH_2\overset{\displaystyle \diagdown\!\!\!\diagup}{\underset{O}{CHCH_2}}$$

and 163 g of polypropylene glycol having an average molecular weight of 1055 were dissolved in 200 cc of CH$_2$Cl$_2$, and 0.3 ml of BF$_3$OEt was added dropwise with heating and refluxing. After completion of the reaction, the reaction mixture was extracted with CH$_2$Cl$_2$ and washed with saturated NaHCO$_3$ and pure water. The organic layer was separated, dried over Na$_2$SO$_4$, filtered and concentrated under reduced pressure at 50° C., giving 120 g of an oily compound.

Example 52

A 20 ml 4-necked flask was charged with 10.75 g (50 mmol) of isomyristyl alcohol of the following formula (1), 11 g of chloroform and 8 drops of boron trifluoride ether complex.

The epoxy (26.3 g, 50 ml) of the following formula (2) was dropwise added at 65° C. over a period of about 50 minutes and stirred with heating at about 65° C. for 6 hours.

After completion of the reaction, the reaction mixture was washed with 30 ml of chloroform and 100 ml of a 5% aqueous NaCO$_3$ solution, dried over anhydrous magnesium sulfate and filtered and the filtrate was concentrated, giving 28 g (yield 74%) of the objective compound.

$$\begin{array}{c} CH_3CH(CH_3)CH_2CH_2CH_2CH_2 \\ | \\ HOCH_2CH \\ | \\ CH_3CH(CH_3)CH_2CH_2 \end{array} \quad (1)$$

$$CF_3CF_2(CF_2CF_2)_{3.5}CH_2\overset{\displaystyle \diagdown\!\!\!\diagup}{\underset{O}{CHCH_2}} \quad (2)$$

Example 53

A 4-necked flask was charged with 100 g of polybuthylene glycol having an average molecular weight of 1358, 101 g of Et$_3$N and 200 cc of MEK. While the mixture was stirred at a predetermined temperature, 80 g of hexafluoropropylene trimer (T-1/T-2=35/65) was added dropwise. After completion of the reaction, the reaction mixture was extracted with S-3 and washed with a 1N aqueous HCl solution and a saturated aqueous NaHCl solution. The organic layer was dried over Na$_2$SO$_4$, filtered and concentrated under reduced pressure at 50° C., giving 115 g of an oily compound (T-1 origin/T-2 origin=35/65).

Example 54

A 4-necked flask was charged with 58 g of the epoxy compound

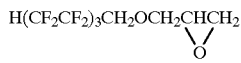

and 150 g of polybutylene glycol having an average molecular weight of 1358, the temperature was elevated and 0.3 ml of $BF_3OEt$ was added dropwise. After completion of the reaction, the reaction mixture was extracted with $CH_2Cl_2$ and washed with saturated $NaHCO_3$ and pure water. The organic layer was separated, dried over $Na_2SO_4$, filtered and concentrated under reduced pressure at 50° C., giving 200 g of an oily compound.

Example 55

A 500-mL autoclave was charged with 73.1 g of isohexanol, 300 mL of dimethyl sulfoxide and 10 g of 85% KOH pellets. While the mixture was stirred at 60° C., tetrafluoroethylene was forced into the autoclave at a pressure of 5 kg/cm$^2$G. After stirring for 20 hours, the reaction mixture was poured in water, extracted with chloroform, washed with a 5% aqueous HCl solution and a 5% $NaHCO_3$ solution and dried over anhydrous magnesium sulfate. The solvent was distilled off under reduced pressure, giving 80.8 g (yield: 88%) of the objective compound.

Example 56

A 500-mL autoclave was charged with 100 g of isomyristyl alcohol, 300 mL of dimethyl sulfoxide and 10 g of 85% KOH pellets. While the mixture was stirred at 60° C., tetrafluoroethylene was forced into the autoclave at a pressure of 5 kg/cm$^2$G. After stirring for 20 hours, the reaction mixture was poured in water and extracted with chloroform and washed with 5% HCl and 5% $NaHCO_3$ and dried over anhydrous magnesium sulfate and the solvent was distilled off under reduced pressure, giving 120.3 g (yield: 82%) of the objective compound.

Example 57

A 500-mL autoclave was charged with 100 g of isoicosyl alcohol, 300 mL of dimethyl sulfoxide and 10 g of 85% KOH pellets. While the mixture was stirred at 60° C., tetrafluoroethylene was forced into the autoclave at a pressure of 5 kg/cm$^2$G. After stirring for 20 hours, the reaction mixture was poured in water and extracted with chloroform and washed with 5% HCl and 5% $NaHCO_3$ and dried over anhydrous magnesium sulfate and the solvent was distilled off under reduced pressure, giving 113.5 g (yield: 85.96%) of the objective compound.

[Physical Properties of the Compounds]

Table 2 shows structural formulas and physical properties of the compounds obtained in Examples 13–53.

TABLE 2

| Example No. | Structural formula | Appearance<br>Specific gravity<br>Viscosity (40° C.)<br>Volume resistivity<br>Pour point |
|---|---|---|
| 13 | $(CF_3)_2CF\diagdown C=C \diagup CF_3$<br>$(CF_3)_2CF \diagup \diagdown O(CH_2)_{17}CH_3$ | Yellow oil<br>1.2242<br>11.7 cst<br>5.65 × 10$^5$ Ωcm<br>0~10° C. |
| 14 | $(CF_3)_2CF\diagdown C=C \diagup CF_3$<br>$(CF_3)_2CF \diagup \diagdown OCH_2CHCH_2CH_2CH(CH_3)$—$CH_2C(CH_3)_3$<br>$\mid$<br>$CH(CH_3)CH_2C(CH_3)_3$ | Yellow oil<br>1.1928<br>30.0 cst<br>1.99 × 10$^{10}$ Ωcm<br>−30~−20° C. |
| 15 | $(CF_3)_2CF\diagdown C=C \diagup CF_3$<br>$(CF_3)_2CF \diagup \diagdown OCH_2CHCH_2CH_2CH(CH_3)$—<br>$\mid$ —$CH_2C(CH_3)_3$<br>$CH(CH_3)CH_2C(CH_3)_3$ | Yellow oil<br>1.2435<br>32.9 cst<br>1.50 × 10$^{10}$ Ωcm<br>−30° C. |
| 16 | $(CF_3)_2CF\diagdown C=C \diagup CF_3$<br>$(CF_3)_2CF \diagup \diagdown O(CHCH_2O)_2CH_3$<br>$\mid$<br>$CH_3$ | Yellow oil<br>1.0888<br>79.5 cst<br>8.74 × 10$^6$ Ωcm<br><−40° C. |

TABLE 2-continued

| Example No. | Structural formula | Appearance Specific gravity Viscosity (40° C.) Volume resistivity Pour point |
|---|---|---|
| 17 | CH$_2$OCF$_2$CFClH<br>\|<br>HCFClCF$_2$OCH$_2$CCH$_2$OCF$_2$CFClH<br>\|<br>CH$_2$OCF$_2$CFClH | Light yellow oil<br>1.617<br>1060.7 cst<br>2.40E + 12 Ωcm<br>−5° C. |
| 18 | CH$_2$OCF$_2$CF$_2$H<br>\|<br>HCF$_2$CF$_2$OCH$_2$CCH$_2$OCF$_2$CF$_2$H<br>\|<br>CH$_2$OCF$_2$CF$_2$H | Colorless oil<br>1.537<br>20.8 cst<br>1.20E + 11 Ωcm<br>−40° C. |
| 19 | CH$_3$CH$_2$C(CH$_2$OCF$_2$CF$_2$H)$_3$ | Light yellow oil<br>1.425<br>18.0 cst<br>1.72E + 11 Ωcm<br>−40/−45° C. |
| 20 | CH$_3$C(CH$_2$OCF$_2$CF$_2$H)$_3$ | Light yellow oil<br>1.469<br>4.0 cst<br>7.14E + 10 Ωcm<br>−45° C. |
| 21 | (CH$_2$)$_2$C(CH$_2$OCF$_2$CF$_2$H)$_2$ | Coloress oil<br>1.332<br>4.0 cst<br>7.14E + 10 Ωcm<br>−45° C. |
| 22 | (CH$_3$)$_2$C(CH$_2$OCF$_2$CFClH)$_2$ | Light yellow oil<br>1.378<br>7.0 cst<br>3.50E + 09 Ωcm<br>−45° C. |
| 23 | (CH$_3$)$_3$CCH$_2$OCF$_2$CFClH | Light yellow oil<br>1.165<br>3.0 cst<br>5.95E + 10 Ωcm<br>−45° C. |
| 24 | HCFClCF$_2$O(CH$_2$)$_6$OCF$_2$CFClH | Brown oil<br>1.367<br>4.0 cst<br>3.51E + 09 Ωcm<br>−45° C. |
| 25 | HCFClCF$_2$OCH(CH$_2$OCF$_2$CFClH)$_2$ | Colorless oil<br>1.572<br>5.0 cst<br>1.15E + 11 Ωcm<br>−40/−45° C. |
| 26 | C(CH$_3$)$_2$(CH$_2$OCF$_2$CFHCF$_3$)$_2$ | Colorless oil<br>1.3832<br>3.7 cst<br>8.5 × 10$^{10}$ Ωcm<br>−35° C. |
| 27 | C(CH$_2$OCF$_2$CFHCF$_3$)$_4$ | Light yellow oil<br>1.6345<br>23.1 cst<br>2.1 × 10$^9$ Ωcm<br>−33° C. |
| 28 | C(HCClFCF$_2$OCH$_2$CHCHJ$_2$)$_2$O<br>OCF$_2$CFClH | Brown oil<br>1.5763<br>35.3 cst<br>3.1 × 10$^{10}$ Ωcm<br>−30° C. |
| 29 | CH$_3$CH$_2$C(CH$_2$OCF$_2$CFClH)$_3$ | Colorless oil<br>1.4862<br>10.3 cst<br>1.1 × 10$^{13}$ Ωcm<br>−40° C. |
| 30 | CH$_3$C(CH$_2$OCF$_2$CFClH)$_3$ | Colorless oil<br>1.5131<br>15.2 cst<br>9.3 × 10$^{11}$ Ωcm |

TABLE 2-continued

| Example No. | Structural formula | Appearance<br>Specific gravity<br>Viscosity (40° C.)<br>Volume resistivity<br>Pour point |
|---|---|---|
| | | −44° C. |
| 31 | RfOCH$_2$CHO(CHCH$_2$O)$_n$CHCH$_2$ORf<br>          \|      \|           \|<br>          OH  CH$_3$    OH | Light yellow oil<br>1.597<br>25.6 cst<br>9.90E + 09 Ωcm<br>−8° C. |
| 32 | (CF$_3$)$_2$CF, CF$_3$, F$_3$C, CF(CH$_3$)$_2$ / C=C / (CF$_3$)$_2$CF, OCH$_2$CHCH$_2$ / C=CCF(CH$_3$)$_2$ / OC=CCF(CH$_3$)$_2$ / F$_3$C  CF(CH$_3$)$_2$ | Light yellow oil<br>1.887<br>81.4 cst<br>5.43E + 11 Ωcm<br>−20° C. |
| 33 | C$_8$F$_{17}$CH$_2$CHCH$_2$O(CH$_2$)$_8$C=CH<br>         \|             H   (CH$_2$)$_7$CH$_3$<br>       OH | Brown oil<br>1.279<br>44.0 cst<br>5.12E + 11 Ωcm<br>5° C. |
| 34 | C$_8$F$_{17}$CH$_2$CH$_2$O(CH$_2$CHO)$_2$H<br>                    \|<br>                   CH$_2$Cl | Light yellow oil<br>1.600<br>67.0 cst<br>9.68E + 08 Ωcm<br>15° C. |
| 35 | C$_8$F$_{17}$CH$_2$CH$_2$O(CH$_2$CHO)$_{10}$H<br>                    \|<br>                CH$_2$(CF$_2$CF$_2$)$_3$—<br>                              —CF(CF$_3$)$_2$ | Yellow oil<br>1.730<br>95.0 cst<br>1.14E + 11 Ωcm<br>−5° C. |
| 36 | C$_8$F$_{17}$CH$_2$CH$_2$O(CH$_2$CHO)$_3$H<br>                  \|<br>              CH$_2$O-nBu | Colorless oil<br>1.279<br>27.0 cst<br>1.08E + 10 Ωcm<br>35° C. |
| 37 | (CF$_3$)$_2$CF(CF$_2$CF$_2$)$_3$CH$_2$CHCH$_2$OCH$_2$—<br>                       \|<br>                     OH    —CH$_2$Cl | Colorless oil<br>1.717<br>42.0 cst<br>4.21E + 09 Ωcm<br>10° C. |
| 38 | (CF$_3$)$_2$CF(CF$_2$CF$_2$)$_3$CH$_2$CHCH$_2$O—<br>                     \|<br>                OH<br>—CH$_2$CHCH$_2$CH$_2$CH(CH$_3$)CH$_2$C(CH$_3$)$_3$<br>       \|<br>    CH(CH$_3$)CH$_2$C(CH$_3$)$_3$ | Colorless oil<br>1.2843<br>73.0 cst<br>1.17 × 10$^{12}$ Ωcm<br>−10∼0° C. |
| 39 | (CF$_3$)$_2$CF(CF$_2$CF$_2$)$_3$CH$_2$CHCH$_2$O—<br>                     \|<br>                OH<br>—CH$_2$CHCH$_2$CH$_2$CH$_2$CH$_2$CH(CH$_3$)CH$_3$<br>    —CH$_2$CH$_2$CH(CH$_3$)CH$_3$ | Colorless oil<br>1.3468<br>40.4 cst<br>7.24 × 10$^{11}$ Ωcm<br>−30∼−20° C. |
| 40 | HCF$_2$CF$_2$O(CH$_2$CHCH$_2$O)$_n$CF$_2$CF$_2$H<br>                 \|<br>              OCF$_2$CF$_2$H | Colorless oil<br>1.517<br>147.7 cst<br>2.50E + 10 Ωcm<br>−30° C. |

TABLE 2-continued

| Example No. | Structural formula | Appearance<br>Specific gravity<br>Viscosity (40° C.)<br>Volume resistivity<br>Pour point |
|---|---|---|
| 41 | $HCF_2CF_2O(CH_2CHCH_2O)_nCF_2CF_2H$<br>$\quad\quad\quad\quad\quad\quad\quad\|$<br>$\quad\quad\quad\quad\quad\quad OCF_2CF_2H$ | Colorless oil<br>1.517<br>146.8 cst<br>1.10E + 11 Ωcm<br>−33° C. |
| 42 | $HClFCCF_2O(CH_2CHCH_2O)_nCF_2CFClH$<br>$\quad\quad\quad\quad\quad\quad\quad\quad\|$<br>$\quad\quad\quad\quad\quad\quad\quad OCF_2CFClH$ | colorless oil<br>1.509<br>116.6 cst<br>8.80E + 08 Ωcm<br>−28° C. |
| 43 | $HClFCCF_2O(CH_2CHCH_2O)_nCF_2CFClH$<br>$\quad\quad\quad\quad\quad\quad\quad\quad\|$<br>$\quad\quad\quad\quad\quad\quad\quad OCF_2CFClH$ | Brown oil<br>1.559<br>192.9 cst<br>8.10E + 10 Ωcm<br>−28° C. |
| 44 | $HClFCCF_2O(CH_2CHCH_2O)_nCF_2CFClH$<br>$\quad\quad\quad\quad\quad\quad\quad\quad\|$<br>$\quad\quad\quad\quad\quad\quad\quad OCF_2CFClH$ | Brown oil<br>1.551<br>231.1 cst<br>3.00E + 10 Ωcm<br>−28° C. |
| 45 | $HCF_2CF_2O(CH_2CHCH_2O)_nCF_2CF_2H$<br>$\quad\quad\quad\quad\quad\quad\quad\|$<br>$\quad\quad\quad\quad\quad\quad OCF_2CF_2H$ | Brown oil<br>1.473<br>425.8 cst<br>5.20E + 09 Ωcm<br>−18° C. |
| 46 | $HCF_2CF_2O(CH_2CHCH_2O)_nCF_2CF_2H$<br>$\quad\quad\quad\quad\quad\quad\quad\|$<br>$\quad\quad\quad\quad\quad\quad OCF_2CF_2H$ | Colorless oil<br>1.528<br>80.0 cst<br>2.27E + 09 Ωcm<br>−35/−40° C. |
| 47 | $C_{20}H_{41}O\quad CF(CF_3)_2 \quad\quad C_{20}H_{41}O\quad CF_3$<br>$\quad\quad\ \ \diagdown C=C\diagup \quad\quad\quad\quad\quad\ \diagdown C=C\diagup$<br>$\quad\quad\ \diagup\quad\quad\diagdown \quad\quad\quad\quad\quad\quad\quad\diagup\quad\quad\diagdown$<br>$\quad CF_3\quad\quad F\quad\quad\quad\quad\quad C_2F_5\quad\quad CF_3$ | Brown oil<br>1.066<br>49.8 cst<br>2.35E + 10 Ωcm<br>−30° C. |
| 48 | $C_{16}H_{33}OC(CF_3)_2OH$ | Light yellow oil<br>1.060<br>9.7 cst<br>1.59E + 10 Ωcm<br>−50° C. |
| 49 | $CF_3\quad C_2F_5 \quad\ C_2F_5\quad CF_3$<br>$\ \ \diagdown C=C\diagup \quad\quad \diagdown C=C\diagup$<br>$\ \diagup\quad\quad\diagdown \quad\quad\quad\diagup\quad\quad\diagdown$<br>$CF_3\quad O(CH_2)_nO\quad CF_3$ | Colorless transparence<br>—<br>—<br>9.90 × 10⁷ Ωcm<br>≦−40° C. |
| 50 | $CF_3\quad\quad\quad\quad\quad\quad\quad\quad\quad OH$<br>$\ \ \diagdown\quad\quad\quad\quad\quad\quad\quad\quad\ \ \|$<br>$\quad\ CF(CF_2CF_2)_nCH_2CHCH_2O\text{---}\!\!\!\!\neg$<br>$\ \ \diagup\quad\quad\quad\quad\quad\quad\quad\quad\quad\quad\quad\quad\ \ \|$<br>$CF_3\quad\quad\quad\quad\quad\quad\quad\quad\text{---}(CHCH_2O)_nCH_3$<br>$\quad\quad\quad\quad\quad\quad\quad\quad\quad\quad\ \ \|$<br>$\quad\quad\quad\quad\quad\quad\quad\quad\quad\ \ CH_3$ | Colorless oil<br>1.249<br>61 cst<br>5.79 × 10⁸ Ωcm<br>−40° C. |
| 51 | $\quad\quad\quad\quad\quad\quad\quad OH$<br>$\quad\quad\quad\quad\quad\quad\quad\ \|$<br>$H(CF_2CF_2)_3CH_2OCH_2CHCH_2O\text{---}\!\!\!\!\neg$<br>$\quad\quad\quad\quad\quad\quad\quad\quad\quad\quad\quad\quad\ \ \|$<br>$\quad\quad\quad\quad\quad\quad\quad\text{---}(CHCH_2O)_nCH_3$<br>$\quad\quad\quad\quad\quad\quad\quad\ \ \|$<br>$\quad\quad\quad\quad\quad\quad\ \ CH_3$ | Oil<br>1.195<br>82 cst<br>1.88 × 10⁸ Ωcm<br>−40~−35° C. |

TABLE 2-continued

| Example No. | Structural formula | Appearance<br>Specific gravity<br>Viscosity (40° C.)<br>Volume resistivity<br>Pour point |
|---|---|---|
| 52 | $CF_3CF_2(CF_2CF_2)_nCH_2CHCH_2OC_{14}H_{29}$<br>                                                               OH | Light yellow oil<br>1.349<br>58.8 cst<br>$1.25E + 13$ Ωcm<br>$-25°$ C. |
| 53 | $(CF_3)_2CF$      $CF_3$<br>     \      /<br>      C=C<br>     /      \<br>$(CF_3)_2CF$    $O(CHCH_2O)_nCH_3$<br>                           $CH_2CH_3$ | Brown oil<br>0.9953<br>79.7 cst<br>$1.33 \times 10^7$ Ωcm<br>$-40°$ C. |
| 54 | $H(CF_2CF_2)_3CH_2OCH_2CHCH_2O$—<br>                           OH<br>                                 —$(CHCH_2O)_nCH_3$<br>                                       $CH_2CH_3$ | Oil<br>1.120<br>108 cst<br>$7.10 \times 10^8$ Ωcm<br>$-40°$ C. |
| 55 | $C_{13}H_{27}$<br>    \<br>     CHCH_2OCF_2CF_2H<br>    /<br>$C_{11}H_{23}$ | Brown oil<br>0.950<br>24.0 cst<br>$2.00E + 12$ Ωcm<br>$-55°$ C. |
| 56 |                      $(CH_3)_2CHCH_2CH_2$<br>                                      \<br>$(CH_3)_2CHCH_2CH_2CH_2CH_2CHCH_2OCF_2$—<br>                                                 —$CF_2H$ | Colorless oil<br>1.051<br>25.4 cst<br>$9.05 \times 10^9$ Ωcm<br>$<-40°$ C. |
| 57 | $C_{10}H_{21}$<br>    \<br>     CHCH_2OCF_2CF_2H<br>    /<br>$C_8H_{17}$ | Colorless oil<br>0.980<br>20.7 cst<br>$6.15 \times 10^{10}$ Ωcm<br>$<-40°$ C. |

[Compatibility Test-1]

The compounds obtained in Examples were tested for compatibility with HFC134a.

The compounds (oils) obtained in Examples were placed in Pyrex test tubes 8 mm in inner diameter and 200 mm long. The tubes were evacuated into a vacuum, cooled with liquid nitrogen and charged with 1 g of a refrigerant, HFC134a (oil/refrigerant ratio 20/80 wt. %). The tubes were then sealed and placed in a thermostat held at a controlled temperature. After the temperature reached an equilibrium, the compounds were visually checked for the compatibility with the refrigerant and the phase separation temperature was determined at a low temperature. Table 3 shows the phase separation temperature at a low temperature.

After compatibility test, the compounds obtained in Examples 49, 50 and 51 were cooled to determine the phase separation temperature at a low temperature but failed to separate into phases even at −50° C.

[Compatibility Test-2]

The compounds obtained in Examples were tested for compatibility with HFC134a/HFC32.

The compounds (oils) obtained in Examples were placed in Pyrex test tubes 8 mm in inner diameter and 200 mm long. The tubes were vacuumed, cooled with liquid nitrogen and charged with 1 g of a refrigerant, HFC134a/HFC32 (70/30 wt. %), (oil/refrigerant ratio 20/80 wt. %). The tubes were then sealed and placed in a thermostat held at a controlled temperature. After the temperature reached an equilibrium, the compounds were visually checked for the compatibility with the refrigerant and the phase separation temperature was determined at a low temperature.

Table 3 shows the phase separation temperature at a low temperature.

[Compatibility Test-3]

The compounds obtained in Examples were tested for compatibility with HFC134a/HFC32/HFC125.

The compounds (oils) obtained in Examples were placed in Pyrex test tubes 8 mm in inner diameter and 200 mm long. The tubes were vacuumed, cooled with liquid nitrogen and charged with 1 g of a refrigerant, HFC 134a/HFC32/HFC125, (40/30/30 wt. %), (oil/refrigerant ratio 20/80 wt. %). The tubes were then sealed and placed in a thermostat held at a controlled temperature. After the temperature reached an equilibrium, the compounds were visually checked for the compatibility with the refrigerant and the phase separation temperature was determined at a low temperature.

Table 3 shows the phase separation temperature at a low temperature.

[Compatibility Test-4]

The compounds obtained in Examples were tested for compatibility with HFC134a/HFC32/HFC23.

The compounds (oils) obtained in Examples were placed in Pyrex test tubes 8 mm in inner diameter and 200 mm long. The tubes were vacuumed, cooled with liquid nitrogen and charged with 1 g of a refrigerant, 134a/HFC32/HFC23 (70/25/5 wt. %), (oil/refrigerant ratio 20/80 wt. %). The tubes were then sealed and placed in a thermostat held at a controlled temperature. After the temperature reached an equilibrium, the compounds were visually checked for the compatibility with the refrigerant and the phase separation temperature was determined at a low temperature.

Table 3 shows the phase separation temperature at a low temperature.

TABLE 3

| | Phase separation temperature (° C.) | | | |
|---|---|---|---|---|
| Refrigerant Example | 134A Test 1 | 32/134A Test 2 | 134A/32/125 Test 3 | 134A/32/23 Test 4 |
| 13 | 0° C. | 0° C. | 0° C. | 0° C. |
| 14 | −10 | 10 | −10 | −10 |
| 15 | ≦−40 | −30 | −40 | −20 |
| 16 | ≦−50° C. | ≦−50° C. | ≦−50° C. | ≦−50° C. |
| 17 | ≦−50 | 0 | −10 | 0 |
| 18 | ≦−50 | ≦−50 | ≦−50 | ≦−50 |
| 19 | ≦−50 | ≦−50 | ≦−50 | ≦−50 |
| 20 | ≦−50 | ≦−50 | ≦−50 | ≦−50 |
| 21 | ≦−50° C. | ≦−50° C. | ≦−50° C. | ≦−50° C. |
| 22 | ≦−50 | ≦−50 | ≦−50 | ≦−50 |
| 23 | ≦−50 | ≦−50 | ≦−50 | ≦−50 |
| 24 | ≦−50 | ≦−50 | ≦−50 | ≦−50 |
| 25 | ≦−50 | ≦−50 | ≦−50 | ≦−50 |
| 26 | ≦−50° C. | ≦−50° C. | ≦−50° C. | ≦−50° C. |
| 27 | ≦−50 | ≦−50 | ≦−50 | ≦−50 |
| 28 | ≦−50 | ≦−50 | ≦−50 | ≦−50 |
| 29 | ≦−50 | ≦−50 | ≦−50 | ≦−50 |
| 30 | ≦−50 | ≦−50 | ≦−50 | ≦−50 |
| 31 | ≦−50° C. | −40° C. | −50° C. | 40° C. |
| 32 | ≦−50 | ≦−50 | ≦−50 | ≦−50 |
| 34 | 10 | 0 | 0 | 0 |
| 35 | ≦−50 | −30 | −50 | −40 |
| 36 | ≦−50° C. | −50° C. | −50° C. | −40° C. |
| 37 | −40 | 0 | 0 | 0 |
| 38 | −10 | −10 | −10 | −10 |
| 39 | −20 | −20 | 20 | −20 |
| 40 | ≦−50 | ≦−50 | ≦−50 | ≦−50 |
| 41 | ≦−50° C. | ≦−50° C. | ≦−50° C. | ≦−50° C. |
| 42 | −30 | −30 | −30 | −30 |
| 43 | ≦−50 | ≦−50 | ≦−50 | ≦−50 |
| 44 | ≦−50 | ≦−50 | ≦−50 | ≦−50 |
| 45 | ≦−50 | ≦−50 | ≦−50 | ≦−50 |
| 46 | ≦−50° C. | ≦−50° C. | ≦−50° C. | ≦−50° C. |
| 48 | 0 | 0 | 0 | 0 |
| 49 | ≦−50 | ≦−50 | ≦−50 | ≦−50 |
| 50 | ≦−50 | ≦−50 | ≦−50 | ≦−50 |
| 51 | ≦−50° C. | ≦−50° C. | ≦−50° C. | ≦−50° C. |
| 52 | 20 | −10 | −20 | 5 |

[Compatibility Test-5]

The compounds prepared in Examples 17, 42 and 53–55 (see Table 2) were tested for the solubility in various common solvents, i.e. methylethylketone (MIBK), n-hexane, toluene, methylene chloride, and i-propanol (IPA).

Table 4 shows the results. A known fluorine-containing polyether (average molecular weight:4500), F(CF$_2$CF$_2$CF$_2$O)$_n$CF$_2$CF$_3$, was also tested as Comparative Example 7 with the results also shown in Table 4.

TABLE 4

| Example | MIBK | Hexane | Toluene | Methylene chloride | IPA |
|---|---|---|---|---|---|
| 17 | A | A | A | A | A |
| 42 | A | A | A | A | A |
| 53 | A | A | A | A | A |
| 54 | A | B | A | A | A |
| 55 | A | B | A | A | A |
| Com. Ex.7 | C | C | C | C | C |

In Table 4, the symbol A represents a solubility of at least 25 wt. %, B a solubility of at least 1 wt. %, and C an insolubility (a solubility of less than 1 wt. %).

[Tape Property Test]

Magnetic coating compositions of the following formula were prepared using the compounds of Examples 17, 42 and 53–55 as lubricants. The compositions thus obtained were applied to a 14 μm-thick polyethylene terephathalate film to a thickness of 4 μm on dry bas dried, calendered and treated at 50° C. for 80 hours. The magnetic film thus obained was cut to a width of 8 mm to provide a 8 mm video tape recorder.

| Formulation of magnetic coating composition | (parts by weight) |
|---|---|
| Co-containing needle-like γ-iron oxide | 100 parts |
| Polyol (1) | 10 parts |
| Vinyl chloride/vinyl acetate copolymer (2) | 10 parts |
| Lubricant | 10 parts |
| Polyisocyanate (3) | 5 parts |
| MIBK | 100 parts |
| Toluene | 100 parts |

Notes:
(1) Nipporan 2304, product of Nippon Urethane Co., Ltd.
(2) VAGH, product of UCC Co., Ltd.
(3) Coronate L, product of Nippon Urethane Co., Ltd.

The coefficient of friction μ of the magnetic tapes thus obtained was determined from the load when the tape was placed at an angle of 90° with one end of the tape under a load of 10 g and the other end thereof pulled at a speed of 10 cm/sec using ISO R468 steel cylinder (R$_0$=25 μm, 100 mm diameter, v=5 cm/sec).

The results are shown below. A known fluorine-containing polyester (average molecular weight:4500), F(CF$_2$CF$_2$CF$_2$O)$_n$CF$_2$CF$_3$, was also tested as the lubricant with the results shown as Comparative Example 8.

| Lubricant | Coefficient of friction |
|---|---|
| Example 17 | 0.23 |
| Example 42 | 0.22 |
| Example 53 | 0.30 |
| Example 54 | 0.25 |
| Example 55 | 0.35 |
| Com. Ex.8 | 0.40 |

The above results show that the abrasion resistance of the magnetic recording medium was increased when the compounds of the present invention were used as lubricants.

What we claim is:

1. A fluorinated hydrocarbon compound having at least one oxygen atom in the molecule and represented by the formula (II)

wherein d is 1 or 2, $R^5$ is selected from the group consisting of $(CF_3)_2CF(CF_2CF_2)_nCH_2CH_2OCH_2CH(OH)CH_2—$ (n=integer of 0–10), $CF_3CF_2(CF_2CF_2)_mCH_2CH_2OCH_2CH(OH)CH_2—$ (m=integer of 0–10), $H(CF_2CF_2)_lCH_2CH_2CH(OH)CH_2—$ (l=integer of 0–10), $(CF_3)_2CF(CF_2CF_2)_kCH_2CH(OH)CH_2—$ (k=integer of 0–10), or $CF_3CF_2(CF_2CF_2)_jCH_2CH(OH)CH_2—$ (j=integer of 0–10)

$(CF_3)_2CF(CF_2CF_2)_aCH_2CH_2—$ (a=integer of 0–10), $CF_3CF_2(CF_2CF_2)_bCH_2CH_2—$ (b=integer of 0–10), or $H(CF_2CF_2)_cCH_2—$ (c=integer of 1–10), $HCF_2CF_2—$, $HCClFCF_2—$, $HCF_2CClF—$, $CF_3CFHCF_2—$, $CF_3CF=CF—$, $CF_2=CFCF_2—$, $CH_3CF_2—$, $(CF_3)_2CHCF_2—$, $HOC(CF_3)_2—$, $Cl(CF_2CClF)_iCFHCClF—$ (i=integer of 1–20)

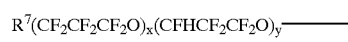

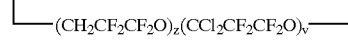

wherein x, y, z, v and w are each an integer of 0 to 100, provided that they can not be zero at the same time, or $R^8(CF(CF_3)CF_2O)_p(CF_2CF_2O)_q(CF_2O)_rR^9—$ wherein p, q and r are each an integer of 0 to 100, provided that they can not be zero at the same time, and when d is 1 $R^6$ is $C_nH_{2n+1}—$ (n=integer of 10–30), $C_mH_{2m-1}—$ (m=integer of 10–30), $C_hH_{2h-3}—$ (h=integer of 10–30), $ClC_lH_{2l}—$ (l=integer of 1–10), $Cl(CH_2)_7CH=CH(CH_2)_8—$ $CH_3(OCH_2CH_2)_k—$ (k=integer of 1–100),

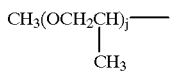

(j=integer of 1–100),

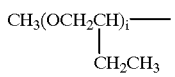

(i=integer of 1–100),

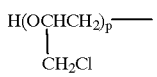

(p=integer of 1–100),

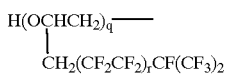

(q=integer of 1–100 and r=integer of 0–10),

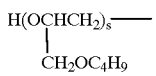

(s=integer of 1–100),
and when d is 2 $R^6$ represents
—$(C_hH_{2h})$— (h=integer of 1–10)

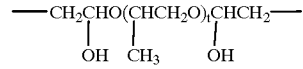

(t=integer of 1–100)
wherein t is an integer of 1 to 100, provided that combinations of $R^5$ and $R^6$ are excluded when $R^5$ is

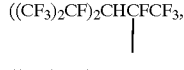

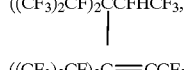

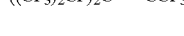

and $R^6$ is —$(CH_2)_4—$.

2. The fluorinated hydrocarbon compound of the formula (II) having at least one oxygen atom in the molecule according to claim 1 wherein $R^5$ is $(CF_3)_2CF(CF_2CF_2)_nCH_2CH_2OCH_2CH(OH)CH_2—$ (n=integer of 0–10), $CF_3CF_2(CF_2CF_2)_mCH_2CH_2OCH_2CH(OH)CH_2—$ (m=integer of 0–10), $H(CF_2CF_2)_lCH_2CH_2CH(OH)CH_2—$ (l=integer of 0–10), $(CF_3)_2CF(CF_2CF_2)_kCH_2CH(OH)CH_2—$ (k=integer of 0–10), or $CF_3CF_2(CF_2CF_2)_jCH_2CH(OH)CH_2—$ (j=integer of 0–10).

3. The fluorinated hydrocarbon compound of the formula (II) having at least one oxygen atom in the molecule according to claim 1 wherein $R^5$ is $(CF_3)_2CF(CF_2CF_2)_aCH_2CH_2$— (a=integer of 0–10),
$CF_3CF_2(CF_2CF_2)_bCH_2CH_2$— (b=integer of 0–10), or
$H(CF_2CF_2)_cCH_2$— (c=integer of 1–10).

4. The fluorinated hydrocarbon compound of the formula (II) having at least one oxygen atom in the molecule according to claim 1 wherein $R^5$ is $HCF_2CF_2$—, $HCClFCF_2$—, $HCF_2CClF$—,
$CF_3CFHCF_2$—, $CF_3CF=CF$—,
$CF_2=CFCF_2$—, $CH_3CF_2$—, $(CF_3)_2CHCF_2$—, $HOC(CF_3)_2$—,
$Cl(CF_2CClF)_iCFHCClF$— (i=integer of 1–20).

5. The fluorinated hydrocarbon compound of the formula (II) having an oxygen atom in the molecule according to claim 1 wherein $R^5$ is

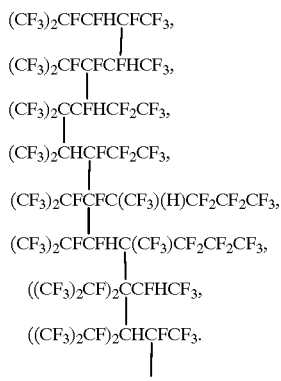

6. The fluorinated hydrocarbon compound of the formula (II) having at least one oxygen atom in the molecule according to claim 1 wherein $R^5$ is

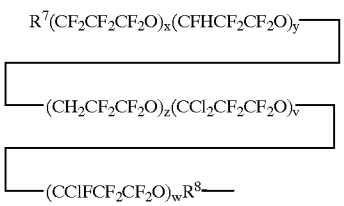

wherein x, y, z, v and w are each an integer of 0 to 100, provided that they can not be zero at the same time, or $R^8(CF(CF_3)CF_2O)_p(CF_2CF_2O)_q(CF_2O)_rR^9$— wherein p, q and r are each an integer of 0 to 100, provided that they can not be zero at the same time, $R^7$ and $R^8$ are each a halogen atom or an alkoxy group having 1 to 3 carbon atoms (which may be partly or fully fluorinated), and $R^9$ is a bifunctional alkyl group, bifunctional alkenyl group, bifunctional alkylether group, or bifunctional alkyl alcohol group having 1 to 5 carbon atoms (which may be partly or fully fluorinated).

7. The fluorinated hydrocarbon compound of the formula (II) having at least one oxygen atom in the molecule according to claim 1 wherein d is 1 and $R^6$ is $C_nH_{2n+1}$— (n=integer of 10–30),
$C_mH_{2m-1}$— (m=integer of 10–30),
$C_hH_{2h-3}$— (h=integer of 10–30), $ClC_lH_{2l}$— (l=integer of 1–10),
$Cl(CH_2)_7CH=CH(CH_2)_8$—.

8. The fluorinated hydrocarbon compound of the formula (II) having at least one oxygen atom in the molecule according to claim 1 wherein d is 1 and $R^6$ is $CH_3(OCH_2CH_2)_k$— (k=integer of 1–100),

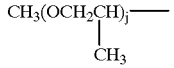

(j=integer of 1–100),

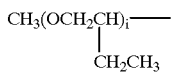

(i=integer of 1–100),

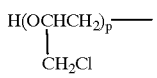

(p=integer of 1–100),

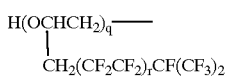

(q=integer of 1–100 and r=integer of 0–10),

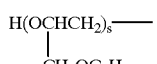

(s=integer of 1–100).

9. The fluorinated hydrocarbon compound of the formula (II) having at least one oxygen atom in the molecule according to claim 1 wherein d is 2 and $R^6$ is —$(C_hH_{2h})$— (h=integer of 1–10)

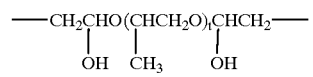

(t=integer of 1–100) wherein t is an integer of 1 to 100, provided that combinations of $R^5$ and $R^6$ are excluded when $R^5$ is

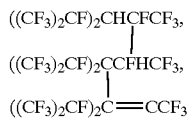

and $R^6$ is —$(CH_2)_4$—.

10. A process for preparing a fluorinated hydrocarbon compound, comprising reacting at least one fluoroolefin or fluoroketone selected from the group consisting of
$CF_2=CF_2$, $CClF=CF_2$, $CF_3CF=CF_2$,
$CH_2=CF_2$, $(CF_3)_2C=CF_2$, $(CF_3)_2C=O$,
$Cl(CF_2CClF)_iCF=CClF$, (i=integer of 1–20),
$CF_3CF=CF_2$, $(CF_3)_2CFCF=CFCF_3$,
$(CF_3)_2C=CFCF_2CF_3$,
$(CF_3)_2CFCF=C(CF_3)CF_2CF_2CF_3$
$((CF_3)_2CF)_2C=CFCF_3$,
$(CF_3)_2C=C(CF_2CF_3)CF(CF_3)_2$,

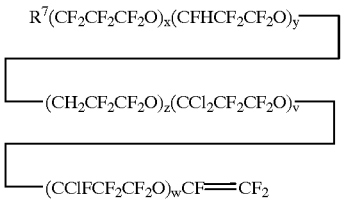

wherein x, y, z, v and w are each an integer of 0 to 100, provided that they can not be zero at the same time, and $R^7$ is a halogen atom or an alkoxy group having 1 to 3 carbon atoms (which may be partly or fully fluorinated), or

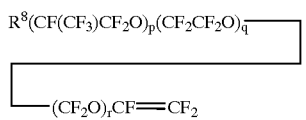

wherein p, q and r are each an integer of 0 to 100, provided that they can not be zero at the same time, and $R^8$ is a halogen atom or an alkoxy group having 1 to 3 carbon atoms (which may be partly or fully fluorinated), with an alcohol represented by the formula $R^6OH$      [IX]

wherein $R^6$ is one of the following substituents:

$C_nH_{2n+1}$— (n=integer of 10–30),
$C_mH_{2m-1}$— (m=integer of 10–30),
$C_hH_{2h-3}$— (h=integer of 10–30),
$ClC_lH_{2l}$— (l=integer of 1–10),
$Cl(CH_2)_7CH=CH(CH_2)_8$—,
$CH_3(OCH_2CH_2)_k$— (k=integer of 1–100),

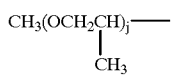

(j=integer of 1–100),

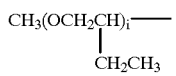

(i=integer of 1–100),

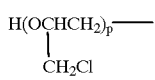

(p=integer of 1–100),

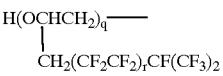

(q=integer of 1–100), or

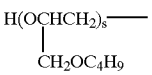

wherein s is an integer of 1 to 100 and r is an integer of 0 to 10.

11. A process for preparing a fluorinated hydrocarbon compound, comprising reacting at least one fluoroolefin or fluoroketone selected from the group consisting of $CF_2=CF_2$, $CClF=CF_2$, $CF_3CF=CF_2$,
$CH_2=CF_2$, $(CF_3)_2C=CF_2$, $(CF_3)_2C=O$,
$Cl(CF_2CClF)_iCF=CClF$ (i=integer of 1–20),
$CF_3CF=CF_2$, $(CF_3)_2CFCF=CFCF_3$,
$(CF_3)_2C=CFCF_2CF_3$,
$(CF_3)_2CFCF=C(CF_3)CF_2CF_2CF_3$
$((CF_3)_2CF)_2C=CFCF_3$,
$(CF_3)_2C=C(CF_2CF_3)CF(CF_3)_2$,

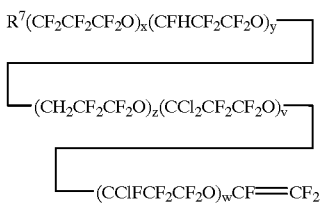

wherein x, y, z, v and w are each an integer of 0 to 100, provided that they can not be zero at the same time, and $R^7$ is a halogen atom or an alkoxy group having 1 to 3 carbon atoms (which may be partly or fully fluorinated), and

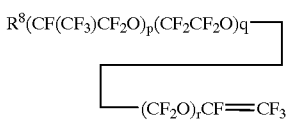

wherein p, q and r are each an integer of 0 to 100, provided that they can not be zero at the same time, and $R^8$ is a halogen atom or an alkoxy group having 1 to 3 carbon atoms (which way be partly or fully fluorinated), with an alcohol represented by the formula $HOR^6OH$      (IX')

wherein $R^6$ is —$(C_hH_{2h})$— (wherein h is an integer of 1 to 10).

12. A process for preparing a fluorinated hydrocarbon compound, comprising reacting a compound represented by the formula

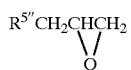

(X)

wherein $R^{5''}$ is
   $(CF_3)_2CF(CF_2CF_2)_nCH_2CH_2O-$ (n=integer of 0–10)
   $CH_3CF_2(CF_2CF_2)_mCH_2CH_2O-$ (m=integer of 0–10)
   $H(CF_2CF_2)_lCH_2-$ (l=integer of 0–10)
   $(CF_3)_2CF(CF_2CF_2)_k-$ (k=integer of 0–10), or
   $CF_3CF_2(CF_2CF_2)_j-$ (j=integer of 0–10)
with an alcohol represented by the formula $R^6OH$      [IX]

wherein $R^6$ is one of the following substituents:
   $C_nH_{2n+1}-$ (n=integer of 10–30)
   $C_mH_{2m-1}-$ (m=integer of 10–30)
   $C_hH_{2h-3}-$ (h=integer of 10–30)
   $ClC_lH_{2l}-$ (l=integer of 1–10)
   $Cl(CH_2)_7CH=CH(CH_2)_8-$
   $CH_3(OCH_2CH_2)_k-$ (k=integer of 1–100)

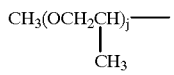

(j=integer of 1–100)

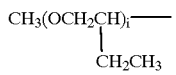

(i=integer of 1–100)

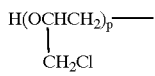

(p=integer of 1–100)

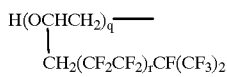

(q=integer of 1–100, and r=integer of 1–10), or

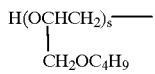

(s=integer of 1–100).

13. A process for preparing a fluorinated hydrocarbon compound, comprising reacting a compound represented by the formula $R^5OH$      [XI]

wherein $R^5$ is one of the following substituents:
   $(CF_3)_2CF(CF_2CF_2)_aCH_2CH_2-$ (a=integer of 0–10)
   $CF_3CF_2(CF_2CF_2)_bCH_2CH_2-$ (b=integer of 0–10), or
   $H(CF_2CF_2)_cCH_2-$ (c=integer of 0–10)
with a compound represented by the formula

(XII)

wherein $R^6$ is $-(C_hH_{2h})-$ (wherein h is an integer of 1 to 10).

14. A lubricant comprising at least one fluorinated hydrocarbon compound having at least one oxygen atom in the molecule and selected from the group consisting of:

a fluorinated hydrocarbon compound having at least one oxygen atom in the molecule and represented by the formula (II)

$(R^5O)_dR^6$ wherein d is 1 or 2, $R^5$ is
   $(CF_3)_2CF(CF_2CF_2)_nCH_2CH_2OCH_2CH(OH)CH_2-$ (n=integer of 0–10),
   $CF_3CF_2(CF_2CF_2)_mCH_2CH_2OCH_2CH(OH)CH_2-$ (m=integer of 0–10),
   $H(CF_2CF_2)_lCH_2CH_2CH(OH)CH_2-$ (l=integer of 0–10),
   $(CF_3)_2CF(CF_2CF_2)_kCH_2CH(OH)CH_2-$ (k=integer of 0–10), or
   $CF_3CF_2(CF_2CF_2)_jCH_2CH(OH)CH_2-$ (j=integer of 0–10)
   $(CF_3)_2CF(CF_2CF_2)_aCH_2CH_2-$ (a=integer of 0–10),
   $CF_3CF_2(CF_2CF_2)_bCH_2CH_2-$ (b=integer of 0–10), or
   $H(CF_2CF_2)_cCH_2-$ (c=integer of 1–10),
   $HCF_2CF_2-$, $HCClFCF_2-$, $HCF_2CClF-$, $CF_3CFHCF_2-$, $CF_3CF=CF-$,
   $CF_2=CFCF_2-$, $CH_3CF_2-$, $(CF_3)_2CHCF_2-$, $HOC(CF_3)_2-$,
   $Cl(CF_2CClF)_iCFHCClF-$ (i=integer of 1–20)

$(CF_3)_2CFCFHCFCF_3$, $(CF_3)_2CFCFCFHCF_3$, $(CF_3)_2CCFHCF_2CF_3$, $(CF_3)_2CHCFCF_2CF_3$, $(CF_3)_2CFCFC(CF_3)(H)CF_2CF_2CF_3$ $(CF_3)_2CFCFHC(CF_3)CF_2CF_2CF_3$, $((CF_3)_2CF)_2CCFHCF_3$, $((CF_3)_2CF)_2CHCFCF_3$

-continued

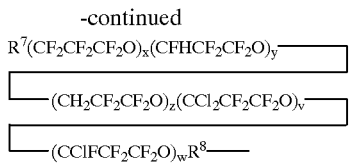

wherein x, y, z, v and w are each an integer of 0 to 100, provided that they can not be zero at the same time, or $R^8(CF(CF_3)CF_2O)_p(CF_2CF_2O)_q(CF_2O)_rR^9$— wherein p, q and r are each an integer of 0 to 100, provided that they can not be zero at the same time, and when d is 1 $R^6$ is $C_nH_{2n+1}$— (n=integer of 10–30),
$C_mH_{2m-1}$— (m=integer of 10–30),
$C_hH_{2h-3}$— (h=integer of 10–30),
$ClC_lH_{2l}$— (l=integer of 1–10),
$Cl(CH_2)_7CH=CH(CH_2)_8$—
$CH_3(OCH_2CH_2)_k$— (k=integer of 1–100),

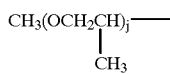

(j=integer of 1–100),

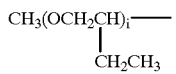

(i=integer of 1–100),

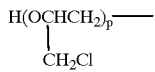

(p=integer of 1–100),

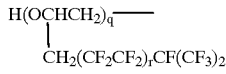

(q=integer of 1–100 and r=integer of 0–10),

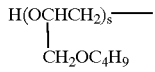

(s=integer of 1–100),
and when d is 2 $R^6$ represents

—$(C_hH_{2h})$— (h=integer of 1–10)

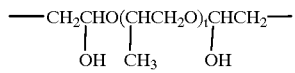

(t=integer of 1–100)
wherein t is an integer of 1 to 100, provided that combinations of $R^5$ and $R^6$ are excluded when $R^5$ is

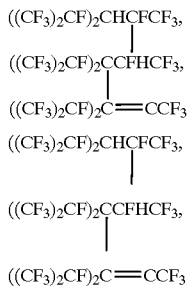

and $R^6$ is —$(CH_2)_4$—.

15. An oil for a refrigerating machine which uses as a refrigerant a hydrogen-containing halogenated hydrocarbon, the oil comprising at least one fluorinated hydrocarbon compound having at least one oxygen atom in the molecule and selected from the group consisting of:

a fluorinated hydrocarbon compound having at least one oxygen atom in the molecule and represented by the formula (II)

$$(R^5O)_dR^6$$

wherein d is 1 or 2, $R^5$ is $(CF_3)_2CF(CF_2CF_2)_nCH_2CH_2OCH_2CH(OH)CH_2$— (n=integer of 0–10),
$CF_3CF_2(CF_2CF_2)_mCH_2CH_2OCH_2CH(OH)CH_2$— (m=integer of 0–10),
$H(CF_2CF_2)_lCH_2CH_2CH(OH)CH_2$— (l=integer of 0–10),
$(CF_3)_2CF(CF_2CF_2)_kCH_2CH(OH)CH_2$— (k=integer of 0–10), or
$CF_3CF_2(CF_2CF_2)_jCH_2CH(OH)CH_2$— (j=integer of 0–10)
$(CF_3)_2CF(CF_2CF_2)_aCH_2CH_2$— (a=integer of 0–10),
$CF_3CF_2(CF_2CF_2)_bCH_2CH_2$— (b=integer of 0–10), or
$H(CF_2CF_2)_cCH_2$— (c=integer of 1–10),
$HCF_2CF_2$—, $HCClFCF_2$—, $HCF_2CClF$—, $CF_3CFHCF_2$—, $CF_3CF=CF$—,
$CF_2=CFCF_2$—, $CH_3CF_2$—, $(CF_3)_2CHCF_2$—, $HOC(CF_3)_2$—,
$Cl(CF_2CClF)_iCFHCClF$— (i=integer of 1–20)

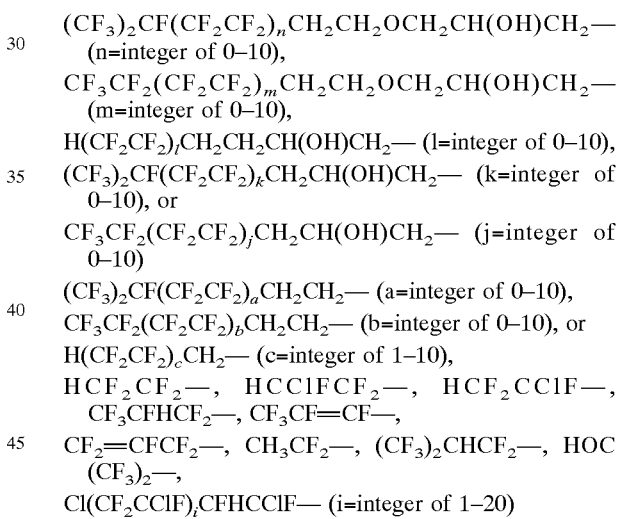

-continued

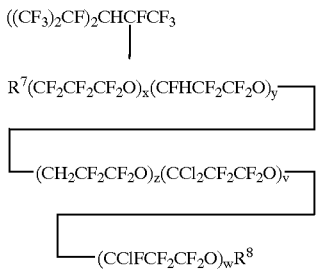

wherein x, y, z, v and w are each an integer of 0 to 100, provided that they can not be zero at the same time, or $R^8(CF(CF_3)CF_2O)_p(CF_2CF_2O)_q(CF_2O)_rR^9$—wherein p, q and r are each an integer of 0 to 100, provided that they can not be zero at the same time, and when d is 1 $R^6$ is $C_nH_{2n+1}$— (n=integer of 10–30),
$C_mH_{2m-1}$— (m=integer of 10–30),
$C_hH_{2h-3}$— (h=integer of 10–30),
$ClC_lH_{2l}$— (l=integer of 1–10),
$Cl(CH_2)_7CH=CH(CH_2)_8$—
$CH_3(OCH_2CH_2)_k$— (k=integer of 1–100),

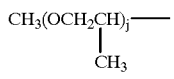

(j=integer of 1–100),

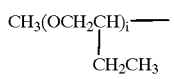

(i=integer of 1–100),

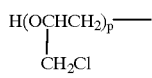

(p=integer of 1–100),

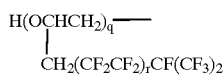

(q=integer of 1–100 and r=integer of 0–10),

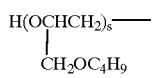

(s=integer of 1–100)
and when d is 2 $R^6$ represents
—$(C_hH_{2h})$— (h=integer of 1–10)

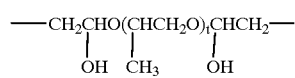

(t=integer of 1–100)
wherein t is an integer of 1 to 100, provided that combinations of $R^5$ and $R^6$ are excluded when $R^5$ is $((CF_3)_2CF)_2CHCFCF_3$, $((CF_3)_2CF)_2CCFHCF_3$, $((CF_3)_2CF)_2C=CCF_3$ and $R^6$ is —$(CH_2)_4$—.

16. A lubricant for magnetic recording media which comprises at least one fluorinated hydrocarbon compound having at least one oxygen atom in the molecule and selected from the group consisting of:

a fluorinated hydrocarbon compound having at least one oxygen atom or a sulfur atom in the molecule and represented by the formula (II)

$$(R^5O)_dR^6$$

wherein d is 1 or 2, $R^5$ is $(CF_3)_2CF(CF_2CF_2)_nCH_2CH_2OCH_2CH(OH)CH_2$— (n=integer of 0–10), $CF_3CF_2(CF_2CF_2)_mCH_2CH_2OCH_2CH(OH)CH_2$— (m=integer of 0–10), $H(CF_2CF_2)_lCH_2CH_2CH(OH)CH_2$— (l=integer of 0–10), $(CF_3)_2CF(CF_2CF_2)_kCH_2CH(OH)CH_2$— (k=integer of 0–10), or $CF_3CF_2(CF_2CF_2)_jCH_2CH(OH)CH_2$— (j=integer of 0–10)

$(CF_3)_2CF(CF_2CF_2)_aCH_2CH_2$— (a=integer of 0–10), $CF_3CF_2(CF_2CF_2)_bCH_2CH_2$— (b=integer of 0–10), or $H(CF_2CF_2)_cCH_2$— (c=integer of 1–10), $HCF_2CF_2$—, $HCClFCF_2$—, $HCF_2CClF$—, $CF_3CFHCF_2$—, $CF_3CF=CF$—, $CF_2=CFCF_2$—, $CH_3CF_2$—, $(CF_3)_2CHCF_2$—, $HOC(CF_3)_2$—, $Cl(CF_2CClF)_iCFCClF$— (i=integer of 1–20)

$(CF_3)_2CFCFHCFCF_3$, $(CF_3)_2CFCFCFHCF_3$, $(CF_3)_2CCFHCF_2CF_3$, $(CF_3)_2CHCFCF_2CF_3$, $(CF_3)_2CFCFC(CF_3)(H)CF_2CF_2CF_3$, $(CF_3)_2CFCFHC(CF_3)CF_2CF_2CF_3$, $((CF_3)_2CF)_2CCFHCF_3$, $((CF_3)_2CF)_2CHCFCF_3$

-continued

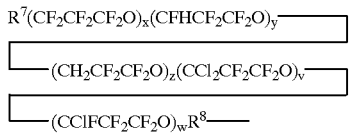

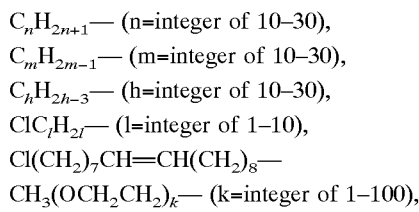

wherein x, y, z, v and w are each an integer of 0 to 100, provided that they can not be zero at the same time, or $R^8(CF(CF_3)CF_2O)_p(CF_2CF_2O)_q(CF_2O)_rR^9$—wherein p, q and r are each an integer of 0 to 100, provided that they can not be zero at the same time, and when d is 1 $R^6$ is $C_nH_{2n+1}$— (n=integer of 10–30), $C_mH_{2m-1}$— (m=integer of 10–30), $C_hH_{2h-3}$— (h=integer of 10–30), $ClC_lH_{2l}$— (l=integer of 1–10), $Cl(CH_2)_7CH=CH(CH_2)_8$—

$CH_3(OCH_2CH_2)_k$— (k=integer of 1–100),

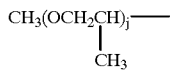

(j=integer of 1–100),

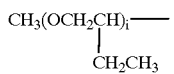

(i=integer of 1–100),

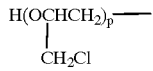

(p=integer of 1–100),

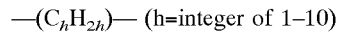

(q=integer of 1–100 and r=integer of 0–10),

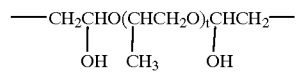

(s=integer of 1–100)

and when d is 2 $R^6$ represents

—$(C_hH_{2h})$— (h=integer of 1–10)

—CH$_2$CHO(CHCH$_2$O)$_t$CHCH$_2$—
   |          |         |
   OH        CH$_3$      OH (t=integer of 1–100)

wherein t is an integer of 1 to 100, provided that combinations of $R^5$ and $R^6$ are excluded when $R^5$ is

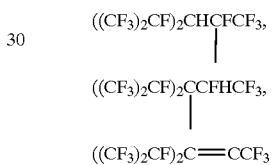

and $R^6$ is —$(CH_2)_4$—.

* * * * *

UNITED STATES PATENT AND TRADEMARK OFFICE
CERTIFICATE OF CORRECTION

PATENT NO. : 6,019,909
DATED : February 1, 2000
INVENTOR(S) : Ide, et. al.

It is certified that error appears in the above-identified patent and that said Letters Patent is hereby corrected as shown below:

Title page, item [22], change "1991" to --1994--.

Signed and Sealed this

Fifth Day of December, 2000

Attest:

Q. TODD DICKINSON

Attesting Officer

Director of Patents and Trademarks